(12) United States Patent
Snow et al.

(10) Patent No.: US 10,894,147 B2
(45) Date of Patent: *Jan. 19, 2021

(54) ADJUSTABLE-LENGTH DRUG DELIVERY BALLOON

(71) Applicant: J.W. Medical Systems Ltd., Palo Alto, CA (US)

(72) Inventors: David W. Snow, San Carlos, CA (US); Patrick H. Ruane, Redwood City, CA (US)

(73) Assignee: J.W. Medical Systems Ltd., Palo Alto, CA (US)

(*) Notice: Subject to any disclaimer, the term of this patent is extended or adjusted under 35 U.S.C. 154(b) by 25 days.

This patent is subject to a terminal disclaimer.

(21) Appl. No.: 16/144,529

(22) Filed: Sep. 27, 2018

(65) Prior Publication Data

US 2019/0022361 A1    Jan. 24, 2019

Related U.S. Application Data

(60) Continuation of application No. 15/183,572, filed on Jun. 15, 2016, now Pat. No. 10,112,034, which is a division of application No. 11/771,929, filed on Jun. 29, 2007, now Pat. No. 9,370,642.

(51) Int. Cl.
*A61M 25/10* (2013.01)
*A61F 2/958* (2013.01)

(52) U.S. Cl.
CPC ............ *A61M 25/10* (2013.01); *A61F 2/958* (2013.01); *A61M 2025/105* (2013.01); *A61M 2025/1068* (2013.01); *A61M 2025/1081* (2013.01)

(58) Field of Classification Search
CPC ............ A61F 2/958; A61M 2025/105; A61M 2025/1068

See application file for complete search history.

(56) References Cited

U.S. PATENT DOCUMENTS

| | | |
|---|---|---|
| 4,824,436 A | 4/1989 | Wolinsky |
| 5,087,244 A | 2/1992 | Wolinsky et al. |
| 5,324,261 A | 6/1994 | Amundson et al. |
| 5,336,178 A | 8/1994 | Kaplan et al. |
| 5,364,356 A | 11/1994 | Hofling |
| 5,549,551 A | 8/1996 | Peacock et al. |
| 5,571,086 A | 11/1996 | Kaplan et al. |
| 5,571,089 A | 11/1996 | Crocker |
| 5,634,901 A | 6/1997 | Alba et al. |
| 5,776,141 A | 7/1998 | Klein et al. |
| 5,855,563 A | 1/1999 | Kaplan et al. |
| 5,868,719 A | 2/1999 | Tsukernik |
| 5,876,374 A | 3/1999 | Alba et al. |

(Continued)

FOREIGN PATENT DOCUMENTS

WO    WO 2009/005933    1/2009

*Primary Examiner* — Diane D Yabut
(74) *Attorney, Agent, or Firm* — Levine Bagade Han LLP

(57) ABSTRACT

A drug or agent coated balloon having a length which is adjustable in vivo is described herein. The balloon is configured to be coated or coatable with one or more drugs where the coating may be applied prior to advancement into a patient body or prior to balloon expansion within the patient body. The length of the expandable portion of the balloon is adjustable to approximate a length of the tissue region to be treated. Moreover, the drug-coated balloon may be used alone or it may be utilized to deploy luminal prostheses having one or more linked or otherwise coupled segments.

20 Claims, 20 Drawing Sheets

(56) References Cited

U.S. PATENT DOCUMENTS

| | | |
|---|---|---|
| 6,139,517 A | 10/2000 | Macoviak et al. |
| 6,409,716 B1 | 6/2002 | Sahatjian et al. |
| 6,685,672 B1 | 2/2004 | Forman |
| 6,837,901 B2 | 1/2005 | Rabkin et al. |
| 6,997,898 B2 | 2/2006 | Forman |
| 7,462,175 B2 | 12/2008 | Chang et al. |
| 2004/0093061 A1 | 5/2004 | Acosta et al. |
| 2005/0095267 A1 | 5/2005 | Campbell et al. |
| 2005/0182361 A1 | 8/2005 | Lennox |
| 2006/0020243 A1 | 1/2006 | Speck et al. |
| 2007/0037865 A1 | 2/2007 | Nunes et al. |
| 2009/0105686 A1 | 4/2009 | Snow et al. |

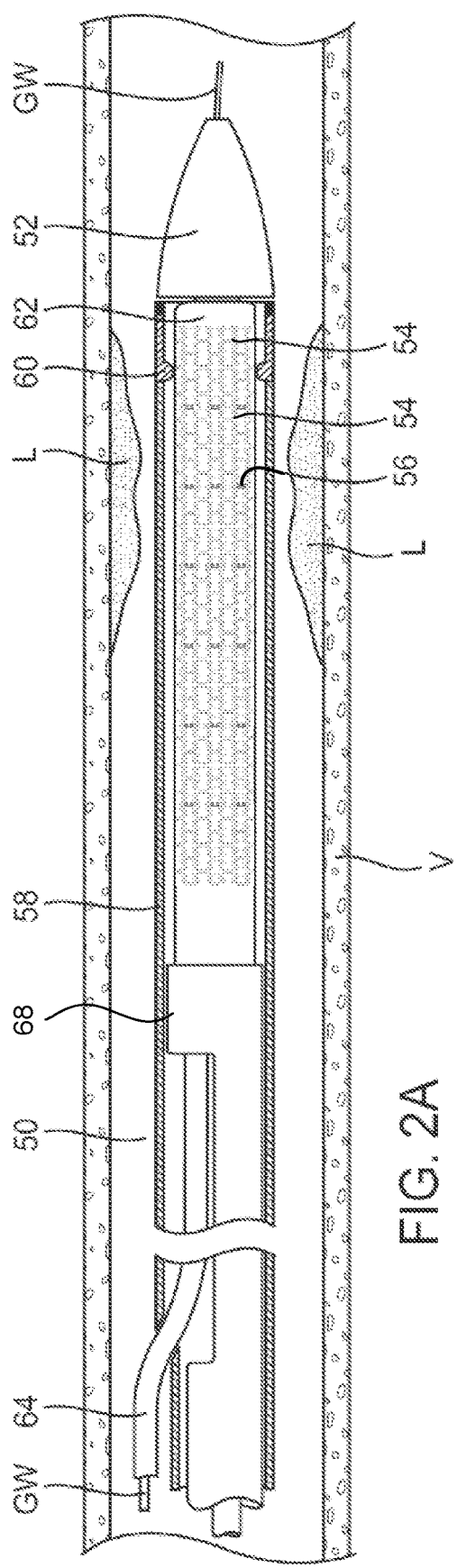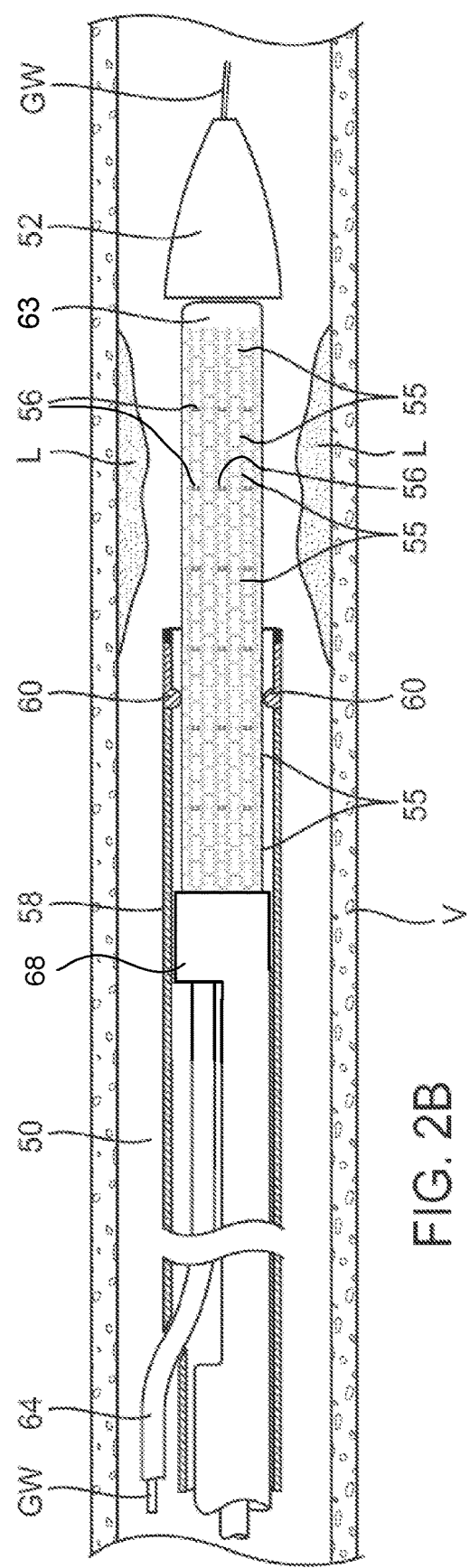

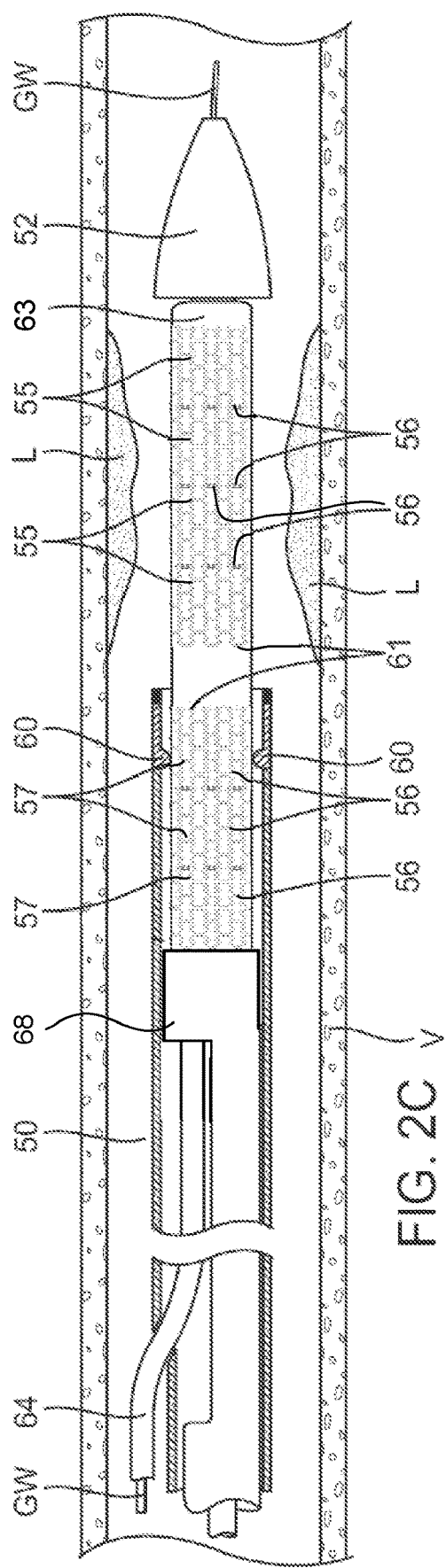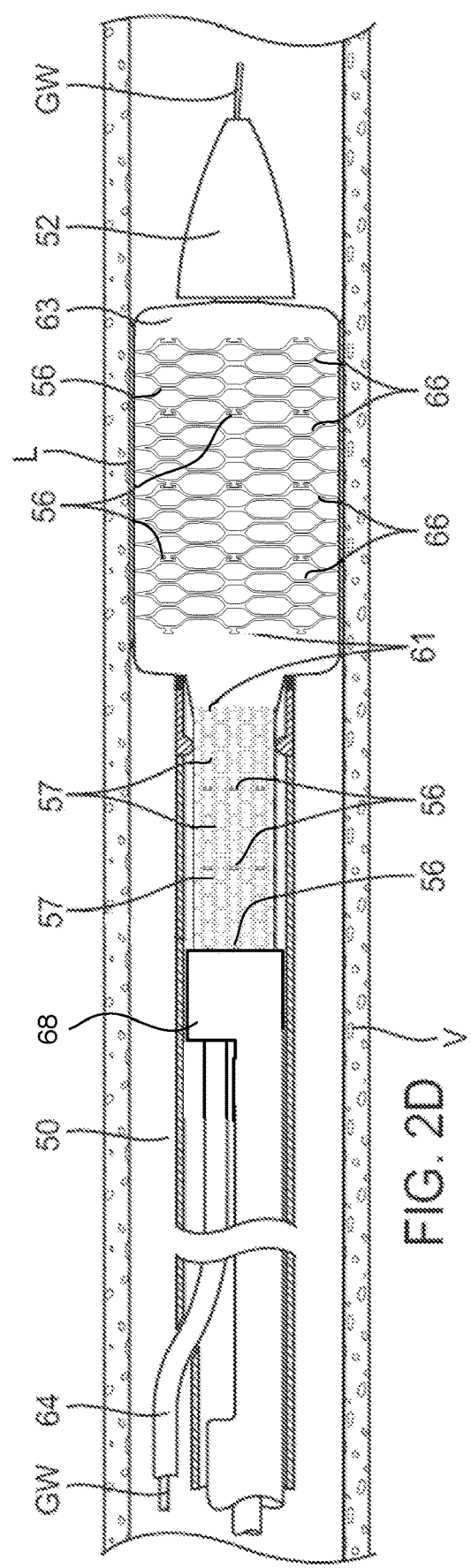

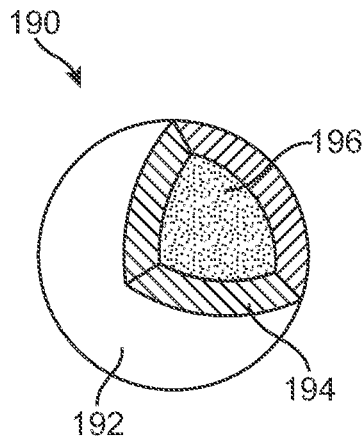
FIG. 16A
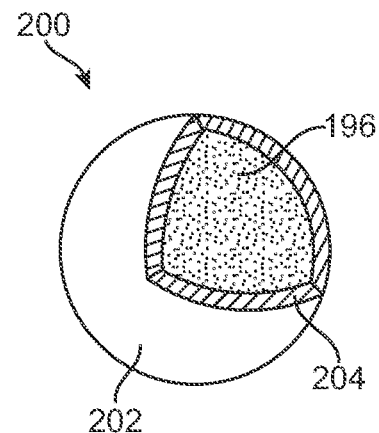
FIG. 16B
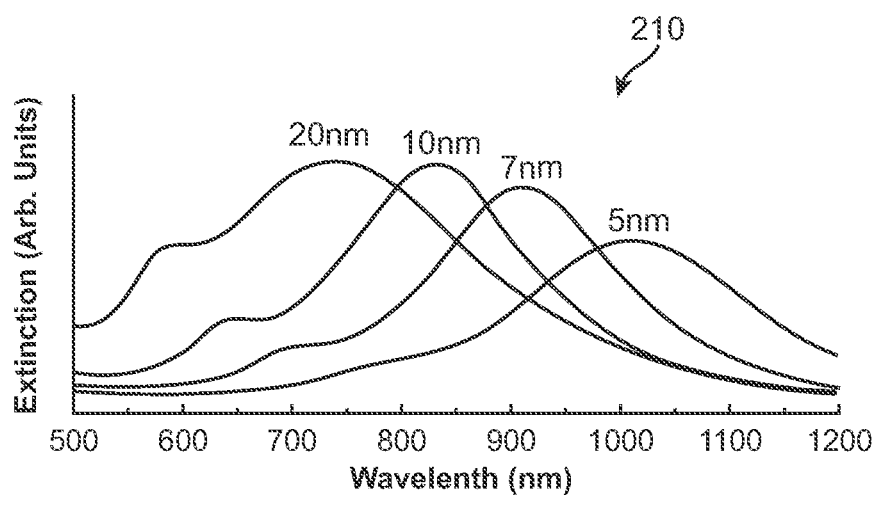
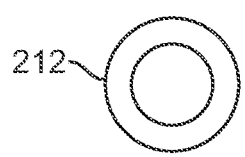
60 nm Core Radius
20 nm Shell
60 nm Core Radius
5 nm Shell
FIG. 17

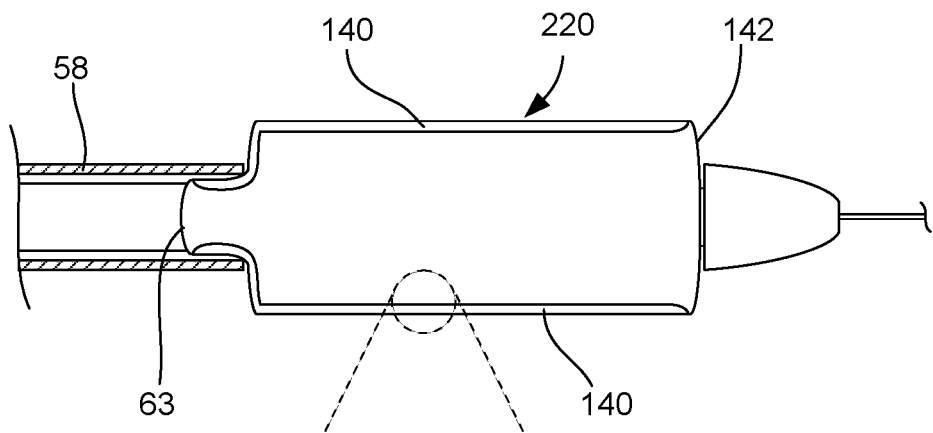
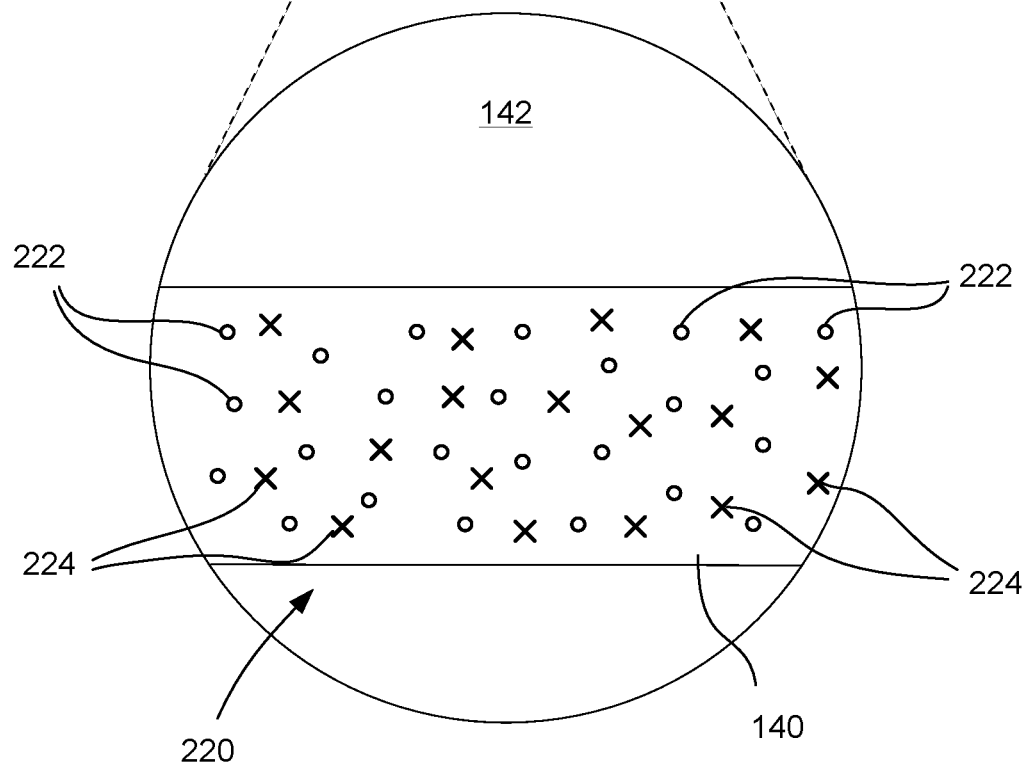
FIG. 18

ADJUSTABLE-LENGTH DRUG DELIVERY BALLOON

CROSS-REFERENCE TO RELATED APPLICATIONS

This application is a continuation of U.S. patent application Ser. No. 15/183,572, filed on Jun. 15, 2016, which is a divisional of U.S. patent application Ser. No. 11/771,929 filed Jun. 29, 2007 (now U.S. Pat. No. 9,370,642), which is incorporated herein by reference in its entirety.

FIELD OF THE INVENTION

The present invention relates generally to medical devices and methods. More specifically, the present invention relates to apparatus and methods for utilizing inflatable balloons having a length adjustable in vivo and coated or coatable with one or more drugs. The drug delivery balloon may be used alone or it may be utilized to deploy luminal prostheses having one or more linked or otherwise coupled segments.

BACKGROUND OF THE INVENTION

In percutaneous transluminal angioplasty ("PTA") and percutaneous transluminal coronary angioplasty ("PTCA") procedures, a dilation balloon is typically advanced intravascularly to a stenosed region and inflated to open the blockage and/or place a stent.

Restenosis, where treated vessels such as coronary arteries tend to become re-occluded (such as following stent implantation), has been addressed by improvements in stent design, delivery systems, and techniques along with the development of drug eluting stents. Typically, a balloon expandable stent is delivered to the coronary arteries using a long, flexible vascular catheter with a balloon on the distal end over which the stent is mounted. The delivery catheter is introduced into the vascular system percutaneously through a femoral or radial artery. Once the catheter is positioned at the target treatment site, the delivery catheter balloon is expanded which correspondingly expands and permanently deforms the stent to a desired diameter. The balloon is then deflated and removed from the vessel, leaving the stent implanted in the vessel at the lesion site.

It may be advantageous to deliver therapeutic agents to a vascular treatment site in combination with balloon angioplasty or stenting. Various methods have also been suggested for delivering drug agents to a dilation site. One technique for delivering such agents is through the use of drug eluting stents which have a coating containing the agent over their exterior. As an alternative, it has been suggested that thin walled flexible balloons having a plurality of small holes could be used to contact the vessel wall and deliver agents upon expansion. Other examples include balloons which are simply coated with a drug and expanded into contact against the treatment site.

However, the length of the treatment region within the vessel may be variable depending upon the patient condition. Because lesion sizes may vary between patients, a balloon catheter having a fixed treatment length for drug delivery may require multiple treatments for a relatively long lesion resulting in increased treatment times and complications. Alternatively, for relatively short lesions, treatment with an excessively long balloon may result in over treatment of the tissue region and unnecessary application or infusion of drugs into the patient system. Although fluoroscopy and angiography may be used to evaluate the lesion prior to catheter insertion, sometimes lesion length cannot be assessed accurately.

It would therefore be desirable to provide drug delivery catheters that could be customized in length at the site of treatment in order to precisely tailor the device to the size of the region to be treated. In addition, it would be desirable if such drug delivery catheters could be used not only for drug delivery, but also for balloon angioplasty and stent delivery as well.

Further, it would be desirable to deliver therapeutic agents and perform balloon angioplasty and/or deliver one or more stents in the same intervention without the need to exchange catheters.

SUMMARY OF THE INVENTION

According to the present invention, variable length inflatable balloons having one or more drugs coated, impregnated, infused, or otherwise coupled to its surface or deliverable through one or more openings over the balloon surface can be utilized to effectively treat to one or more variable length treatment sites during a single interventional procedure. The drug coated balloon can be utilized alone or in combination with one or more stents or stent segments. In preferred embodiments, the length of the deployed stent can be varied depending upon the length of the lesion to be treated, the number of stent segments deployed into a vessel may be selected by the operator at the site of treatment. Additional aspects of the luminal prosthesis delivery system are described in U.S. patent application Ser. No. 10/306,813 filed Nov. 27, 2002 (U.S. Patent Publication 2003/0135266 A1); U.S. patent application Ser. No. 10/637,713 filed Aug. 8, 2003 (U.S. Patent Publication 2004/0098081 A1); U.S. patent application Ser. No. 10/738,666 filed Dec. 16, 2003 (U.S. Patent Publication 2004/0186551 A1); U.S. patent application Ser. No. 11/104,305 filed Apr. 11, 2005 (U.S. Patent Publication 2006/0229700 A1); and U.S. application Ser. No. 11/148,545 filed Jun. 8, 2005 (U.S. Patent Publication 2006/0282147 A1), the full disclosures of which are hereby incorporated by reference.

According to the invention, an inflatable balloon having a variably expandable length may have one or more drug agents disposed upon the entire length of the balloon or simply a portion of the balloon depending upon the desired treatment results. Once the catheter has been desirably positioned proximate or adjacent to the lesion or vessel wall to be treated, the sheath may be retracted relative to the catheter body (alternatively, catheter body and balloon may be advanced distally relative to the sheath) by a distance sufficient to expose a desired length of the balloon to treat the tissue region of interest. As the sheath is retracted a selected distance (as determined by the user), a portion of the balloon remains unexpanded and contained within the sheath while an exposed portion of the balloon is expanded to allow for targeted treatment of a selected length of the vessel wall.

Depending upon the length of the lesion and/or tissue regions to be treated, the sheath may be retracted to expose an appropriate length of the balloon for expansion. Avoiding overexposure of the balloon allows for treatment of the targeted tissue region of interest and may prevent excess drugs from being applied to the tissue wall. The inflatable balloon itself may be coated, impregnated, or infused with one or more drugs for enhancing treatment of the vessel. Drugs or agents which inhibit restenosis may be coated or otherwise placed upon the balloon surface or impregnated or infused within the balloon structure. Alternatively, such drugs may be delivered through various drug delivery mechanisms (as described herein below) via the balloon. Examples of such drugs and agents may include, e.g., Rapamycin, Everolimus, Paclitaxel, analogs, prodrugs, or derivatives of the aforementioned such as Biolimus A9® (Biosensors International), or other suitable agents. Alternatively, other types of drugs or therapeutic materials may be coated, impregnated, infused, or delivered via the balloon, such as antibiotics, thrombolytics, platelet inhibitors and anti-platelet agents, anti-thrombotics, anti-inflammatories, cytotoxic agents, anti-proliferative agents, endothelial cell attractors, promoters or seeding agents, vasodilators, gene therapy agents, radioactive agents, immunosuppressants, chemotherapeutics and/or stem cells, or combinations thereof.

In another variation, the retractable sheath may define a lumen having one or more openings for depositing one or more agents over the balloon. In other variations, the one or more agents may be delivered through the sheath interior rather than through such openings. This variation may utilize a balloon which is pre-coated with a drug prior to advancement in the patient body or a balloon which is uncoated until just before the balloon is expanded in vivo within the vessel. Once the catheter has been positioned proximate or adjacent to the vessel region to be treated, one or more drugs (e.g., drugs or agents which inhibit restenosis) may be infused through the lumen such that the drug passes through the one or more openings. The openings may be varied in a number of different configurations and locations along the sheath. Once the desirable length of the balloon is determined depending upon the length of the vessel wall to be treated, the sheath may be pulled proximally relative to the balloon while infusing the drug or drugs through the lumen and openings such that the drug is deposited upon a surface of the balloon.

Other variations for a variably expandable balloon includes a balloon having a plurality of openings or pores defined over the surface of the balloon along its length. When unexpanded, the openings or pores remain closed along the balloon to prevent the leakage of any drugs; however, when the sheath is retracted at least partially, the openings or pores may expand into an open configuration along just the expanded portion of the balloon to allow for the infusion and release of the drugs from the widened openings.

In one example for delivering and placing a selected number of stent segments expanded via the variably expandable balloon coated with a drug or agent, once the appropriate number of stent segments has been determined for adequately treating the lesion, the sheath may be retracted to expose the desired number of stent segments. As the stent segments are expanded by the balloon into contact against the vessel walls, the expanded portion of the balloon may also contact the vessel wall to deposit the drug from the balloon surface onto the vessel wall. In another variation, one or more additional agents may be infused and placed onto the balloon surface in vivo for application upon the vessel wall and/or stent segments. For example, a first drug, e.g., a restenosis inhibitor such as Rapamycin, Paclitaxel or any of the other such drugs mentioned herein, may be placed upon the balloon and expanded into contact against the vessel wall while deploying the expanded stent segments. The sheath may be placed back over the deflated balloon and a second drug, e.g., a thrombolytic or anti-platelet drug, may be infused and deposited upon the balloon surface. The sheath may be retracted a second time to allow the balloon to expand into contact against the stent and vessel wall to deposit the second drug upon the interior of the stent and/or the vessel wall. This technique may be used alternatively with the porous balloon having a plurality of openings defined over its surface.

In yet another variation, an expandable balloon having a first agent may be expanded to first apply the agent upon the vessel wall prior to expanding the stent segments. The balloon may be coated with a first drug and the stent segments may be initially positioned on the catheter proximal to the balloon. The sheath may be retracted a desired distance sufficient to expose the balloon length for treating the lesion and the balloon may be expanded to contact the lesion and vessel wall thereby delivering the drug thereto. Alternatively, rather than having the balloon initially coated with the first drug, the balloon may be coated by infusing the drug through the retractable sheath.

In either case, once the exposed length of balloon has been expanded into contact with the vessel wall, the balloon may be deflated leaving the first drug disposed upon the vessel wall. The balloon may be retracted into the sheath and the stent segments may then be pushed distally over the balloon via a pusher and the sheath may be retracted again to expose the appropriate number of stent segments to be expanded against the lesion. The balloon is then inflated to expand the stent segments; optionally, the stent segments may be coated with the same or different drug than that delivered by the balloon. With the stent segments and the vessel wall treated with the first drug, the balloon is again retracted within the sheath and a second drug may be infused via the sheath for deposition upon the deflated balloon surface. As the sheath is retracted again to expose the balloon having a second drug coated upon the exposed balloon surface, the balloon may be expanded again to contact the vessel wall and to deposit the second drug upon the tissue surface. With the vessel wall and expanded stent segments treated with both the first and second drugs, the catheter may be repositioned for treating another tissue region.

In yet another example for treatment, the variably expandable drug coated balloon may be utilized to treat a previously deployed restenosing stent. A catheter system having a drug coated balloon may be advanced into the restenosing region of the vessel and sized to expose the balloon to a desirable length which approximates the length of the restenosed region. The balloon may then be expanded to dilate the vessel and to apply the drug onto the tissue wall. With the treatment completed, the balloon may be deflated and the catheter withdrawn from the region leaving the deployed stent and vessel cleared of the stenosis and further leaving the drug deposited upon the vessel wall and stent to further inhibit or prevent restenosis.

The variably expanded balloon may alternatively utilize a polymeric, or other carrier, coating disposed upon its surface for delivering the one or more drugs against the tissue region. Polymeric materials may include, e.g., poly(lactide) (PLA), poly(glycolic acid) (P GA), poly(lactide-co-glycolide) (PLGA), and other polyhydroxyacids, polyethylene glycol (PEG), poly(caprolactone), polycarbonates, polyamides, polyanhydrides, polyamino acids, polyortho esters, polyacetals, degradable polycyanoacrylates and degradable polyurethanes, etc. Examples of natural polymers and materials include proteins such as albumin, collagen, fibrin, fibrinogen, hydroxyapatite (HAp), and synthetic polyamino acids, and polysaccharides such as alginate, heparin, and other naturally occurring biodegradable polymers of sugar units, etc. Other examples of polymeric materials are described in further detail in U.S. application Ser. No. 11/142,788 filed May 31, 2005 (U.S. Patent Publication US 2006/0271151 A1), which is incorporated herein by reference in its entirety. Non-polymeric carrier materials include, e.g., hydrogels, sugars, proteins, ceramics, and powdered metals, among others. The carrier coating may be mixed, infused, or coated with any of the one or more of the drugs mentioned above for application against the vessel wall to be treated.

The variably expanded balloon catheter, in one variation, may generally comprise a balloon catheter with a sheath positioned over the balloon and which is axially movable with respect thereto, wherein a length of an expandable portion of the balloon is adjustable by positioning the sheath along the balloon so that the expandable portion is exposed while a non-expandable portion is covered by the sheath and constrained from expansion therewith, and at least one agent disposable upon at least the expandable portion of the balloon. The agent disposed upon the balloon may include any of the agents mentioned herein.

In utilizing the balloon catheter described herein, one method of treating a region of a vessel wall may generally comprise positioning the inflatable balloon of the catheter in proximity or adjacent to the region of vessel wall, adjusting a position of the sheath with respect to the balloon such that an exposed portion of the balloon is coextensive with the region of vessel wall while a second portion of the balloon is covered by the sheath, and expanding the exposed portion of the balloon such that at least one agent disposed upon the exposed portion of the balloon contacts the region of vessel wall.

BRIEF DESCRIPTION OF THE DRAWINGS

FIG. 2A is a side view of a luminal prosthesis delivery system with multiple stent segments mounted on a delivery catheter and positioned in a vessel, at a target lesion site.

FIG. 2B is a side view illustrating a group of stent segments selected for deployment.

FIG. 2C is a side view illustrating the stent segments selected for deployment separated from the remaining stent segments.

FIG. 2D is a side view illustrating the selected stent segments being radially expanded while the remaining stent segments are left behind on the delivery catheter.

FIGS. 16A and 16B illustrate perspective views of nanoshells having various outer shell thicknesses.

FIG. 17 shows a graph of the optical resonances of metal nanoshells having various ratios of core radius to shell thickness.

FIG. 18 shows an adjustably inflatable balloon having a hydrogel or carrier coating with a concentration of nanoparticles and agents contained therein.

DETAILED DESCRIPTION OF THE INVENTION

Figure 1:
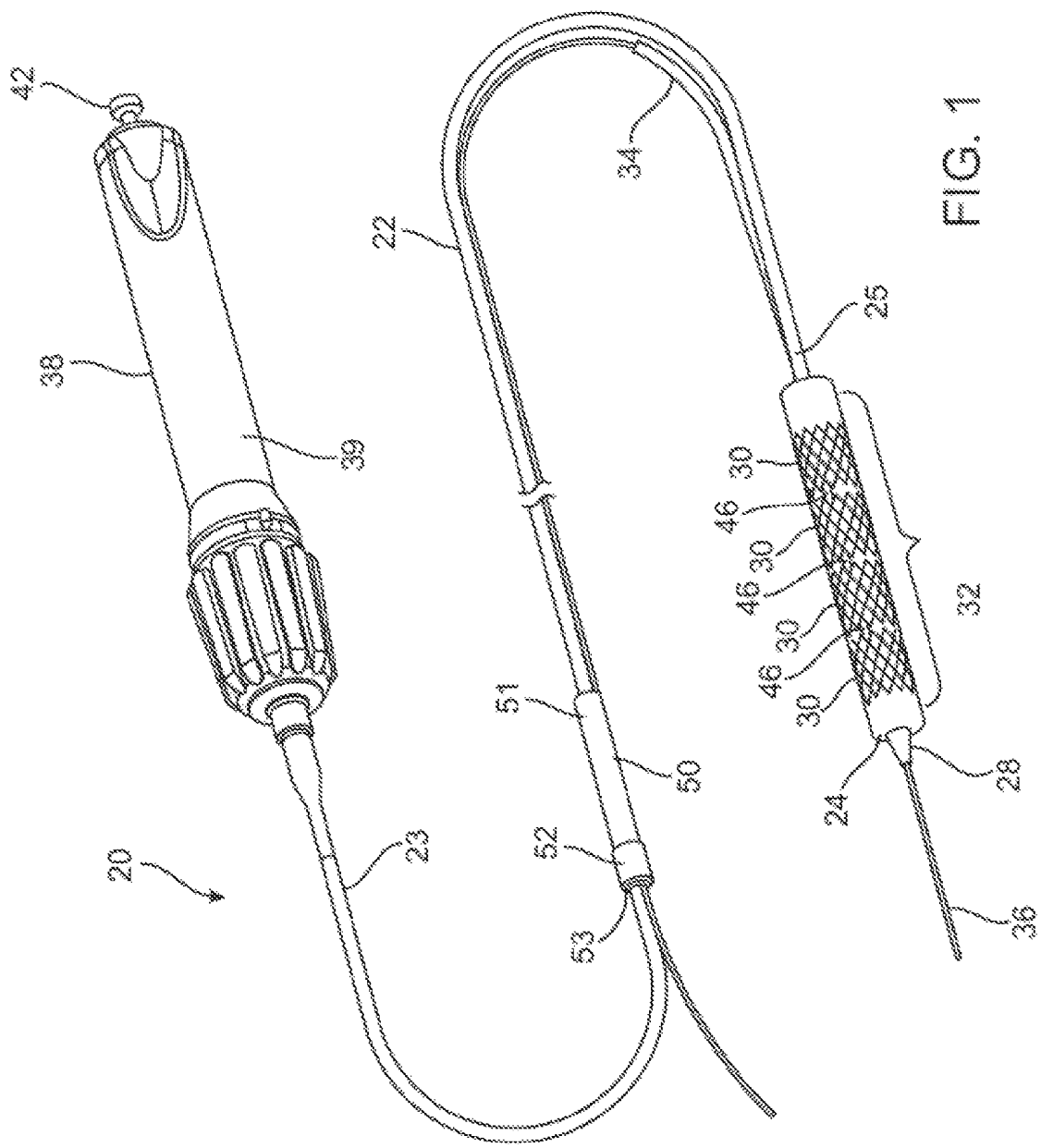
FIG. 1 shows a perspective view of a luminal prosthesis delivery system composed of multiple stent segments arranged axially along a delivery catheter.

An example of a luminal prosthesis delivery system 20 which may be utilized with the one or more stent segments described herein is illustrated in the perspective assembly view of FIG. 1. Luminal prosthesis delivery system 20 generally comprises a catheter shaft 22 with an outer sheath 25 slidably disposed over an inner shaft (not shown). An inflatable balloon 24 is mounted on the inner shaft and is exposed by retracting sheath 25 relative to the inner shaft. A tapered nosecone 28, composed of a soft elastomeric material to reduce trauma to the vessel during advancement of the delivery system is attached distally of the inflatable balloon 24. A luminal prosthesis 32 comprises a plurality of separable stent segments 30 mounted over the inflatable balloon 24 for expansion. A guidewire tube 34 is slidably positioned through sheath 25 proximal to the inflatable balloon 24. A guidewire 36 is positioned slidably through guidewire tube 34, inflatable balloon 24 and nosecone 28 and extends distally thereof.

A handle 38 is attached to a proximal end 23 of the sheath 25. The handle performs several functions, including operating and controlling the catheter body 22 and the components in the catheter body. Various embodiments of the handle 38 along with details concerning its structure and operation are described in U.S. patent application Ser. No. 10/746,466 filed Dec. 23, 2003 (U.S. Patent Publication 2005/0149159 A1), the full disclosure of which is hereby incorporated by reference.

Handle 38 includes a housing 39 which encloses the internal components of the handle 38. The inner shaft is preferably fixed to the handle, while the outer sheath 25 is able to be retracted and advanced relative to handle 38. An adaptor 42 is attached to handle 38 at its proximal end and is fluidly coupled to the inner shaft in the interior of the housing of handle 38. The adaptor 42, e.g., which may be a luer connector, is configured to be fluidly coupled with an inflation device which may be any commercially available balloon inflation device such as those sold under the trade name INDEFLATOR™ manufactured by Abbot (formerly Guidant Corporation of Santa Clara, Calif.). The adaptor is in fluid communication with the inflatable balloon 24 via an inflation lumen in the inner shaft (not shown) to permit inflation of the inflatable balloon 24.

The outer sheath 25 and guidewire 36 each extend through a slider assembly 50 located on the catheter body 22 at a point between its proximal and distal ends. The slider assembly 50 is adapted for insertion into and sealing with a hemostasis valve, such as on an introducer sheath or guiding catheter, while still allowing relative movement of the outer sheath 25 and guidewire 36 relative to the slider assembly 50. The slider assembly 50 includes a slider tube 51, a slider body 52, and a slider cap 53.

The outer sheath 25 may be composed of any of a variety of biocompatabile materials, such as but not limited to, a polymer such as PTFE, FEP, polyimide, or PEBAX® (Arkema France Corp., France), may be reinforced with a metallic or polymeric braid to resist radial expansion of inflatable balloon 24, and/or the like. Inflatable balloon 24 may be formed of a compliant or semi-compliant polymer such as PEBAX®, Nylon, polyurethane, polypropylene, PTFE or other suitable polymer. Compliance of the polymer may be adjusted to provide optimal inflation and stent expansion. Additional aspects of the luminal prosthesis delivery system are described in U.S. patent application Ser. No. 10/306,813 filed Nov. 27, 2002 (U.S. Patent Publication 2003/0135266 A1); U.S. patent application Ser. No. 10/637,713 filed Aug. 8, 2003 (U.S. Patent Publication 2004/0098081 A1); U.S. patent application Ser. No. 10/738,666 filed Dec. 16, 2003 (U.S. Patent Publication 2004/0186551 A1); U.S. patent application Ser. No. 11/104,305 filed Apr. 11, 2005 (U.S. Patent Publication 2006/0229700 A1); and U.S. application Ser. No. 11/148,545 filed Jun. 8, 2005 (U.S. Patent Publication 2006/0282147 A1), the full disclosures of which are hereby incorporated by reference.

The luminal prosthesis 32 may be composed of one or more prosthetic stent segments 30 which are disposed over an inflation balloon 24. Each stent segment may range from about 2-30 mm in length, more typically about 2-20 mm in length, and preferably being about 2-10 mm in length and less than 7 mm in additional preferred embodiments. Usually 2-50, more typically 2-25 and preferably 2-10 stent segments 30 may be positioned axially over the inflation balloon 24 and the inflation balloon 24 has a length suitable to accommodate the number of stent segments. Stent segments 30 may be positioned in direct contact with an adjacent stent segment or a space may exist in between segments. One or more coupling elements 46 may optionally link the adjacent stent segments 30 together, as described in further detail below. Furthermore, the stent segments 30 may be deployed individually or in groups of two or more at one or multiple treatment sites within the vessel lumen.

Prosthetic stent segments 30 may be composed of a malleable metal so they may be plastically deformed by inflation balloon 24 as they are radially expanded to a desired diameter in the vessel at the target treatment site. The stent segments 30 may also be composed of an elastic or superelastic shape memory alloy such as Nitinol so that the stent segments 30 self-expand upon release into a vessel by retraction of the outer sheath 25. In this case, an inflation balloon 24 is not required but may still be used for pre- and/or post-dilatation of a lesion or augmenting expansion of the self-expanding stent segments. Other materials such as biocompatible polymers may be used to fabricate prosthetic stent segments and these materials may further have bioabsorbable or bioerodable properties.

Stent segments 30 may have any of a variety of common constructions, such as but not limited to those described in U.S. patent application Ser. No. 10/738,666 filed Dec. 16, 2003, which was previously incorporated by reference. Constructions may include, for example, closed cell constructions including expansible ovals, ellipses, box structures, expandable diamond structures, etc. In addition, the closed cells may have complex slotted geometries such as H-shaped slots, I-shaped slots, J-shaped slots, etc. Suitable open cell structures include zigzag structures, serpentine structures, and the like. Such conventional stent structures are well described in the patent and medical literature. Specific examples of suitable stent structures are described in the following U.S. Patents, the full disclosures of which are incorporated herein by reference: U.S. Pat. Nos. 6,315,794; 5,980,552; 5,836,964; 5,421,955; and 4,776,337.

Moreover, prosthetic stent segments 30 may be coated, impregnated, infused or otherwise coupled with one or more drugs that inhibit restenosis, such as Rapamycin, Everolimus, Paclitaxel, analogs, prodrugs, or derivatives of the aforementioned such as Biolimus A9® (Biosensors International), or other suitable agents, preferably carried in a durable or bioerodable polymeric carrier. Alternatively or additionally, stent segments 30 may be coated with other types of drugs or therapeutic materials such as antibiotics, thrombolytics, anti-thrombotics, anti-inflammatories, cytotoxic agents, anti-proliferative agents, endothelial cell attractors or promoters, vasodilators, gene therapy agents, radioactive agents, immunosuppressants, chemotherapeutics and/or stem cells, or combinations thereof. Such materials may be coated over all or a portion of the surface of stent segments 30, or stent segments 30 may include apertures, holes, channels, or other features in which such materials may be deposited.

FIGS. 2A to 2D illustrate one example for delivering one or more stent segments in a vessel utilizing the delivery system described above. In FIG. 2A, a partial cross-sectional side view of a luminal prosthesis delivery system 50 is introduced into a vessel V and advanced to the site of a lesion L. The delivery system 50 may have multiple stent segments 54 mounted on a delivery catheter 62 with one or more of the stent segments 54 optionally having at least one coupling element 56 present between the adjacent stent segments. The delivery catheter has a soft nose cone 52, a guidewire tube 64 and an outer sheath 58. A stent valve or separation element 60 disposed on the outer sheath 58 helps separate stent segments 54 selected for delivery from those remaining on the delivery catheter 62. Additionally, a guidewire GW passes through the guidewire tube 64 and exits the delivery catheter from the nose cone 52.

The stent valve or separation element 60 may be mounted to the end or interior of sheath 58 and may be spaced proximally from the distal end of sheath 58 a distance equal to the length of about ½ to 1 stent segments. Stent valve or separation element 60 may comprises an annular ridge configured to frictionally engage stent segments 54 to facilitate control of the spacing between those segments to be deployed distally of sheath 58 and those to be retained within sheath 58. Usually, the stent valve (separation element) is a polymeric (e.g., silicone or urethane) or metallic material and is soft, compliant and resilient enough to provide adequate friction against stent segments 54. Stent valve 50 may also comprise any of the structures described in U.S. patent application Ser. No. 10/412,714 filed Apr. 10, 2003 (U.S. Pat. Pub. No. 2004/0093061 A1), which is incorporated herein by reference.

In FIG. 2B, sheath 58 is retracted a desired distance such that those stent segments 55 selected for deployment are exposed from the outer sheath 58. Because stent segments 55 are slidably positioned over expandable member or balloon 63, a pusher 68 which is axially slidable relative to balloon 63 engages stent segments 55 and maintains their position on balloon 63 as sheath 58 is retracted. In order to move stent segments 55 relative to balloon 63, pusher 68 may be pushed distally to advance stent segments 55 over expandable member or balloon 63 or pusher 68 may be held in a stationary position while expandable member 63 is drawn proximally relative to stent segments 55.

In either case, sheath 58 is axially movable relative to expandable member 63, pusher 68, and stent segments 55 and sheath 58 may be repositioned proximally or distally to selectively expose a desired length of the expandable member and stent segments thereon according to the length of the lesion L to be treated. In preferred embodiments, sheath 58 has a radiopaque marker (not shown) at its distal end, and a second radiopaque marker is located near the distal end of expandable member 63, thus allowing fluoroscopic observation of the exposed length of expandable member 63 and stent segments thereon distal to sheath 58. Further details are shown and described in U.S. patent application Ser. No. 10/746,466 filed Dec. 23, 2003 (U.S. Pat. Pub. No. 2005/0149159 A1), which is incorporated herein by reference.

With the desired number of stent segments 55 selected, sheath 58 may be retracted proximally relative to expandable member 63. Stent valve 60 engages the distal most stent segment 55 within sheath 58 so that pusher 68 and the stent segments within sheath 58 are retracted along with the sheath 58 relative to expandable member 62. This separates stent segments 55 exposed distally of sheath 58 from stent segments 57 held within sheath 58, as illustrated in FIG. 2C. Various other aspects of the construction of delivery catheter and stent segments are described in further detail in U.S. patent application Ser. No. 10/637,713 filed Aug. 8, 2003 (U.S. Patent Publication 2004/0098081 A1), which has been incorporated above by reference.

As illustrated, the stent segments 55 positioned along the delivery catheter 62 may slide freely relative to one another prior to expansion. Because the individual stent segments 55 in their unexpanded configuration are disconnected or uncoupled from one another, the delivery catheter 62 may retain its flexibility, particularly when advanced through tortuous regions of a patient's anatomy. Moreover, the uncoupled stent segments facilitate the separation and release of adjacent stent segments to be expanded, as illustrated in FIG. 2C.

Optionally, stent segments 55 may have coupling mechanisms 56 adapted to link or interconnect upon stent segment expansion. Although the stent segments are disconnected or uncoupled from one another when in their unexpanded shape, they remain aligned with respect to one another such that the complementary portions of one or more coupling mechanisms 56 formed between adjacent stent segments become engaged upon stent expansion, as described in further detail below. Stent segments may accordingly be coupled together by expansion of the balloon or other expandable member.

In FIG. 2D, balloon 63 on the delivery catheter 62 is inflated, radially expanding stent segments 66 which are exposed outside sheath 58. Once the balloon 63 is expanded, the expanded stent segments 66 may optionally become secured to one another upon expansion by coupling mechanisms 56 between adjacent stent segments which securely interlock the segments to one another by taking advantage of the changing geometry of the stents 66 during expansion. The complementary portions of the coupling mechanism 61 between the expanded stent segment 66 and unexpanded stent segment 57 may be seen. With the stent segments 66 expanded against the lesion L and secured to one another, the balloon 63 may be deflated and the delivery system 50 removed from the vessel or moved to the site of another lesion and the procedure repeated.

Figure 3A:
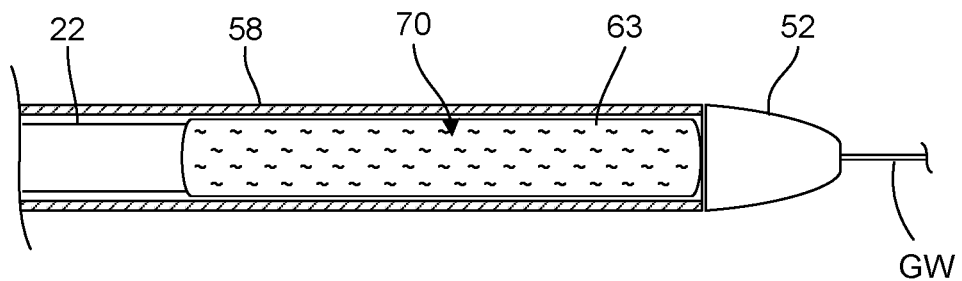
FIG. 3A shows a variation of an inflatable balloon having a variably expandable length in its unexpanded state with one or more drug agents disposed upon the surface of the balloon.
Figure 3B:
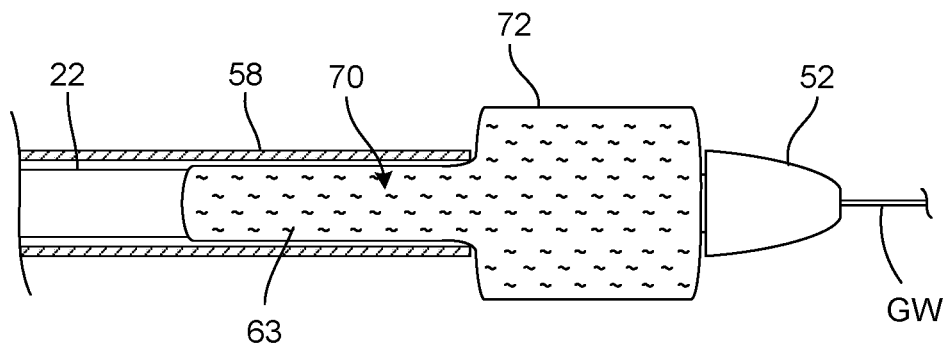
FIG. 3B shows the retractable sheath at least partially retracted such that the expandable length of the balloon may be varied depending upon the length of the vessel to be treated.

FIG. 3A shows a partial cross-sectional view of one variation of an inflatable balloon 63 having a variably expandable length in its unexpanded state with one or more drug agents 70 disposed upon the surface of the balloon. In this variation, the stent segments have been omitted for clarity although the balloon 63 may be used alone, as also described below in further detail. Additionally, the one or more drug agents 70 may be disposed upon the entire length of the balloon 63 or simply a portion of the balloon 63 depending upon the desired treatment results. Retractable sheath 58 is shown as covering or disposed over balloon 63 for delivery. Once the catheter has been desirably positioned proximate or adjacent to the lesion or vessel wall to be treated, sheath 58 may be retracted relative to catheter body 22 (alternatively, catheter body 22 and balloon 63 may be advanced distally relative to sheath 58) by a distance sufficient to expose a desired length of the balloon 63 to treat the tissue region of interest, as shown in FIG. 3B. As the sheath 58 is partially retracted (as determined by the user), a portion of balloon 63 remains unexpanded and contained within sheath 58 while an exposed portion of balloon 63 is expanded 72 to allow for targeted treatment of a selected length of the vessel wall.

Moreover, the exposed portion of the balloon that is expanded against the selected length of vessel wall may be maintained in position for a sustained period of time, e.g., anywhere between 10 seconds to 10 minutes or preferably between 30 seconds to 150 seconds or more preferably about 60 seconds, to ensure the adequate application of the one or more drug agents into or upon the tissue. This time may vary, of course, depending upon the type of vessel being treated as well as the condition of the vessel anatomy. Moreover, the type of agent being applied may also factor into the period of time that the expanded portion of the balloon is contacted against the tissue wall.

Figure 3C:
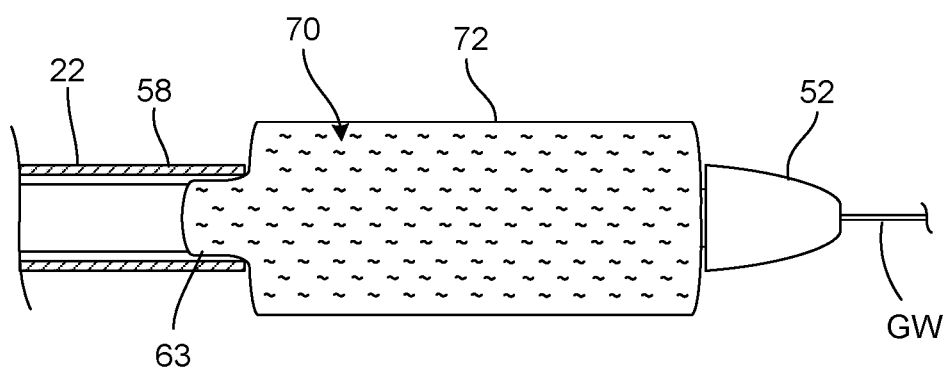
FIG. 3C illustrates the sheath further retracted enabling a longer length of the drug-coated balloon to be expanded.

Depending upon the length of the lesion and/or tissue regions to be treated, sheath 58 may be retracted to expose an appropriate length of the balloon 63 for expansion. Avoiding overexposure of the balloon 63 allows for treatment of the targeted tissue region of interest and may prevent excess drugs from being applied to the tissue wall and/or trauma to healthy areas of the tissue wall as well. FIG. 3C shows the sheath 58 further retracted to expose a longer length of the balloon 63 for expansion if a longer region of vessel wall requires treatment. It should be noted that this allows treatment of two or more lesions of different lengths using a single device in a single intervention, without need to remove or exchange catheters.

Adjustable length balloons, as described herein, having one or more drugs or agents deposited upon its surface for application against vessels walls may be particularly useful for applications within the peripheral vessels, which include but are not limited to vessels such as the, e.g., carotid, brachial, iliac, femoral, renal, popliteal or other arteries. Drug-eluting stents, which have shown dramatic improvements over bare metal stents in treating coronary disease, have not to date had strong clinical success in treating the peripheral vasculature. Thus, the use of coated adjustable length balloons may enable the application of sufficient levels of drugs or agents within the targeted region of the peripheral vessel.

As previously mentioned with respect to the stent segments 30, the inflatable balloon 63 itself may be coated, impregnated, or infused with one or more drugs for enhancing treatment of the vessel. Drugs or agents which inhibit restenosis may be deposited, coated or otherwise placed upon the balloon 63 surface or impregnated or infused within the balloon structure. Alternatively, such drugs may be delivered through various drug delivery mechanisms (as described herein below) via the balloon. Examples of such drugs and agents may include, e.g., Rapamycin, Everolimus, Paclitaxel, analogs, prodrugs, or derivatives of the aforementioned such as Biolimus A9® (Biosensors International), or other suitable agents. Alternatively, other types of drugs or therapeutic materials may be coated, impregnated, infused, or delivered via the balloon 63, such as antibiotics, thrombus inhibitors and anti-platelet drugs, thrombolytics, anti-thrombotics, anti-inflammatories, cytotoxic agents, anti-proliferative agents, endothelial cell attractors or promoters, vasodilators, gene therapy agents, radioactive agents, immunosuppressants, chemotherapeutics and/or stem cells, or combinations thereof.

In applying the drugs or agents upon the tissue walls, the time of application against the tissue wall as well as the amount of the drug or agent carried upon the balloon will vary in part upon the type of drug or agent being applied. For example, for a balloon 63 coated with the agent Paclitaxel, the balloon surface may have a dosage of 2.5 to 3 micrograms/mm$^2$ which may be applied over the period of time, e.g., anywhere between 10 seconds to 10 minutes or preferably between 30 seconds to 150 seconds or more preferably about 60 seconds, against the tissue wall.

Figure 4A:
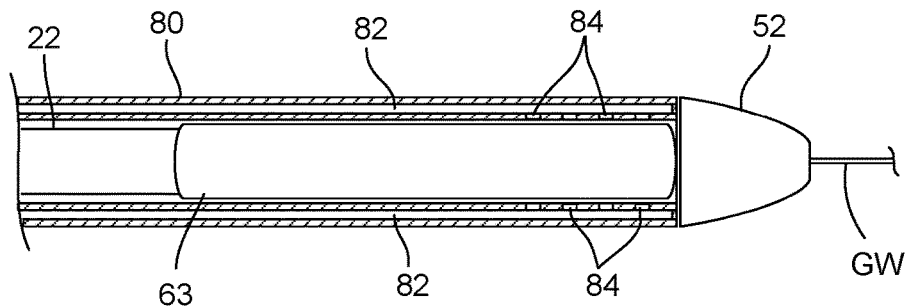
FIG. 4A shows a partial cross-sectional view of another variation of a retractable sheath having an annular lumen defined therethrough with a plurality of openings for infusing one or more agents over the balloon.

In another variation, FIG. 4A shows a partial cross-sectional view of a retractable sheath 80 having lumen 82 defined therethrough with a plurality of openings 84 for depositing one or more agents 86 over the balloon 63. Lumen 82 may be defined as an annular lumen or multiple lumens defined in the wall of sheath 80. The proximal end of lumen 82 is in fluid communication with a reservoir containing the one or more agents to be disposed upon the balloon surface. The reservoir may comprise a syringe, pump, or other suitable container and source of pressure for delivery of liquid agents. This variation may utilize a balloon 63 which is pre-coated with a drug prior to advancement in the patient body or a balloon 63 which is uncoated until just before the balloon 63 is expanded in vivo within the vessel.

Figure 4B:
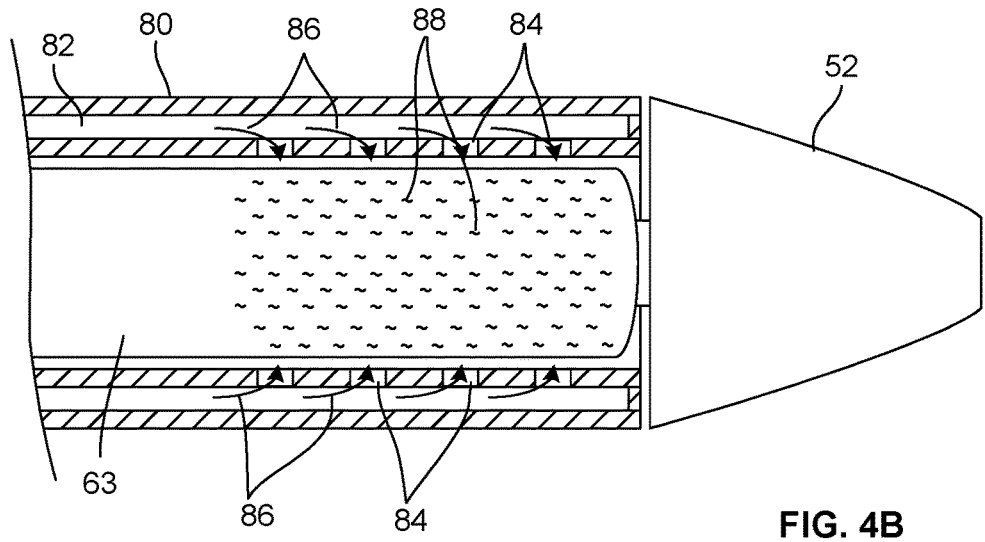
FIGS. 4B and 4C illustrates a partial cross-sectional view of an agent being infused through the openings onto the balloon surface while the sheath is retracted proximally.
Figure 4C:
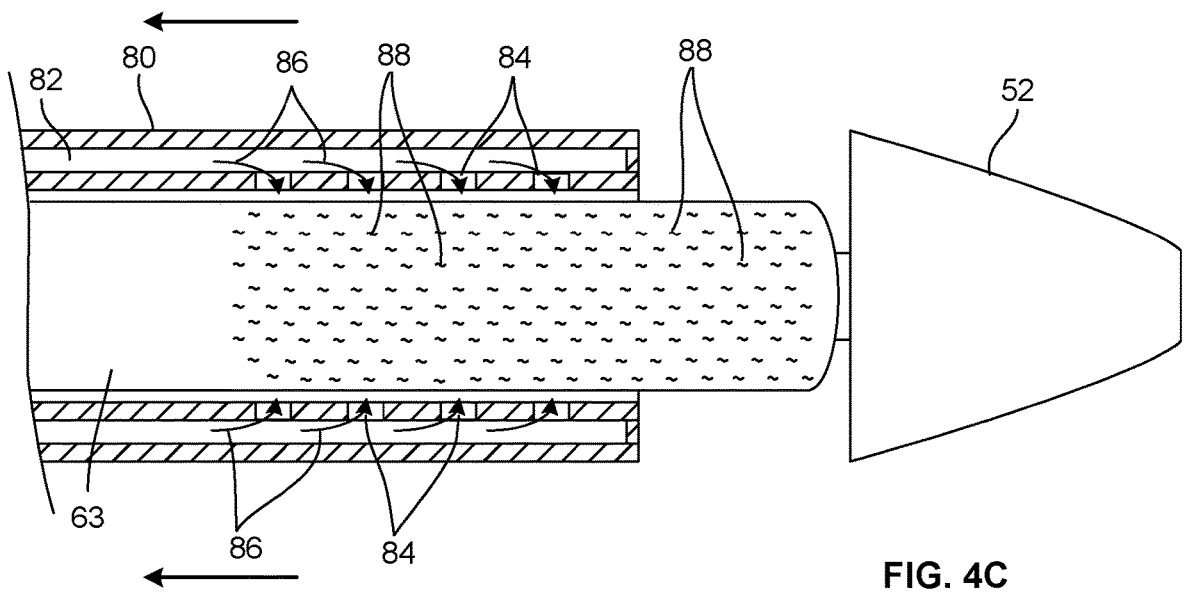

As illustrated in the partial cross-sectional views of FIGS. 4B and 4C, once the catheter has been positioned proximate or adjacent to the vessel region to be treated, one or more drugs 86 (e.g., drugs or agents which inhibit restenosis) may be infused through lumen 82 such that the drug 86 passes through one or more openings 84 which may be defined along the inner surface of sheath 80. This variation illustrates the openings 84 defined near a distal end of sheath 80. Once the desirable length of the balloon 63 is determined depending upon the length of the vessel wall to be treated, sheath 80 may be pulled proximally relative to balloon 63 while infusing the drug or drugs 86 through lumen 82 and openings 84 such that the drug 86 is deposited 88 upon a surface of the balloon 63. As sheath 80 is retracted, as shown by the arrows in FIG. 4C, drug 86 may be continually infused and deposited 88 upon the balloon surface until the desired length of the balloon 63 has been exposed by sheath 80, whereupon infusion of the drug 86 may be ceased such that the drug is deposited 88 upon the portion of the balloon 63 to be expanded while leaving the remainder of the unexpanded balloon uncoated.

Figure 4D:
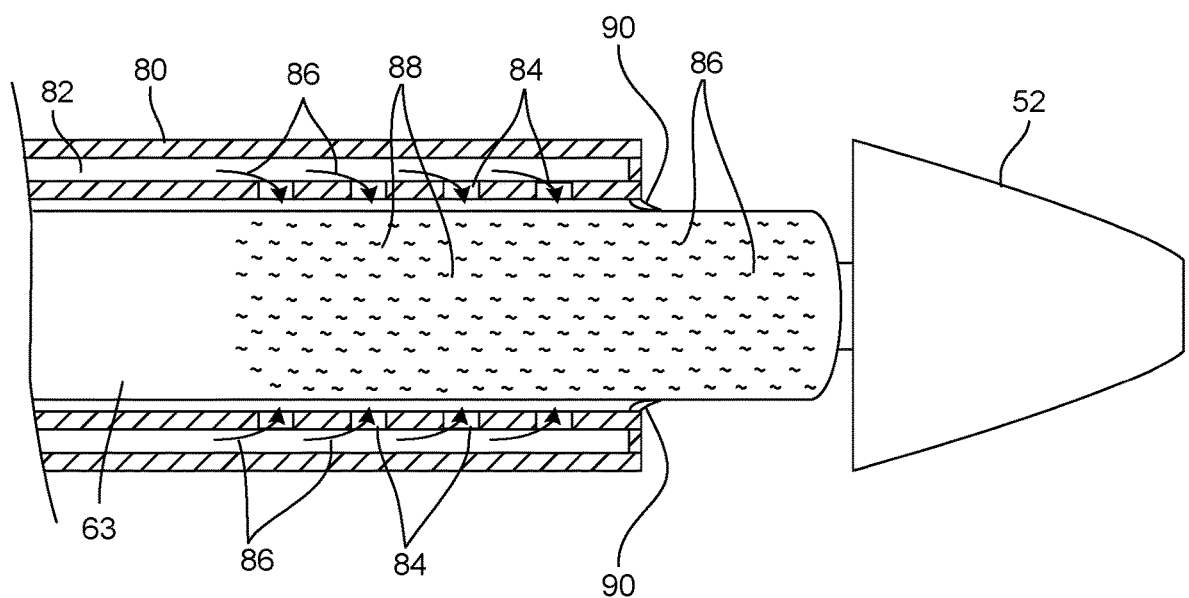
FIG. 4D illustrates a variation of the retractable sheath incorporating a seal which can slide along the balloon surface and inhibit or prevent the release of excess drugs or agents when applied along the balloon.

FIG. 4D illustrates another variation of the retractable sheath 80 which incorporates a seal 90 which seals and slides along the balloon surface to inhibit or prevent the release of excess drugs or agents 86 when delivered via lumen 82. Additionally, seal 90 may facilitate even coating and spreading of the drug over the balloon surface prior to expansion such that the coating may be uniformly applied. The seal 90 can be fabricated from a variety of relatively soft, compliant materials, such as polymers, and it may be configured in a variety of shapes, from a compliant annular ring to an inflatable ring.

Figure 5A:
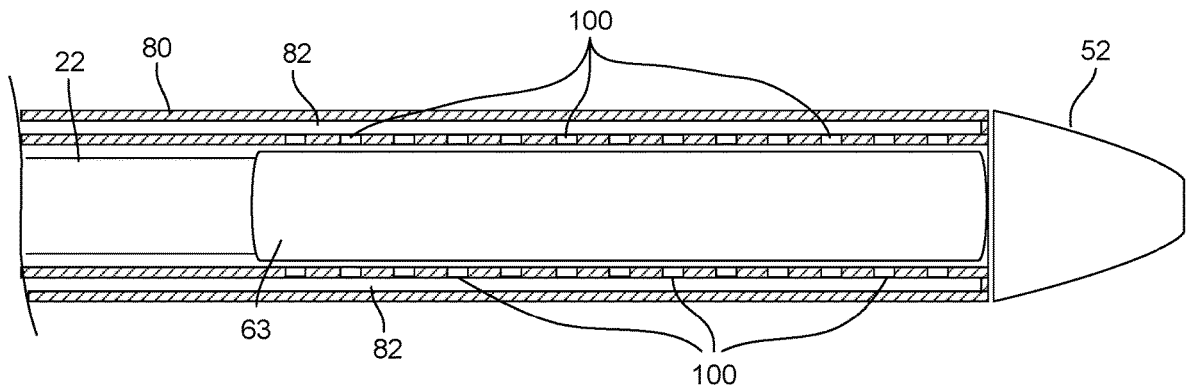
FIGS. 5A to 5C show alternative variations of sheaths having different configurations for positioning of the openings for drug infusion upon the balloon surface.

As mentioned above, the openings through which the drug may be infused upon the balloon surface may be varied in a number of different configurations. FIG. 5A shows a variation where a plurality of openings 100 may be defined on the inner surface of the sheath 80 and extending along a length of the sheath 80 which matches a length of the balloon 63. When infusing the drugs upon the balloon surface prior to expansion against the vessel wall, the entire length of the balloon 63 may be infused simultaneously although just a portion of the balloon 63 may be selectively expanded depending upon the treatment length of the vessel wall.

Figure 5B:
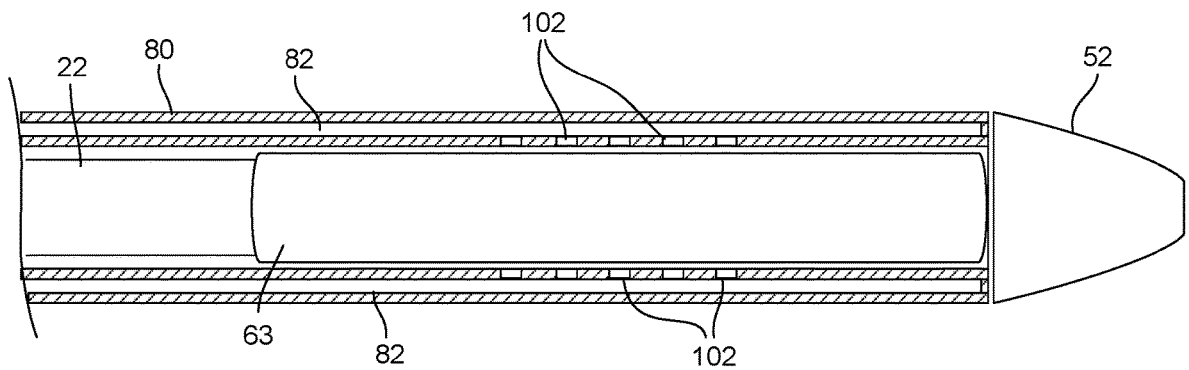

FIG. 5B shows another variation in the partial cross-sectional view of sheath 80 having a plurality of openings 102 defined along the sheath 80 corresponding to a central section of the balloon 63 when the sheath 80 is in its closed configuration with respect to the balloon 63. In this variation, the drugs may be infused upon the balloon 63 from the central section of the balloon 63 and proximally therefrom.

Figure 5C:
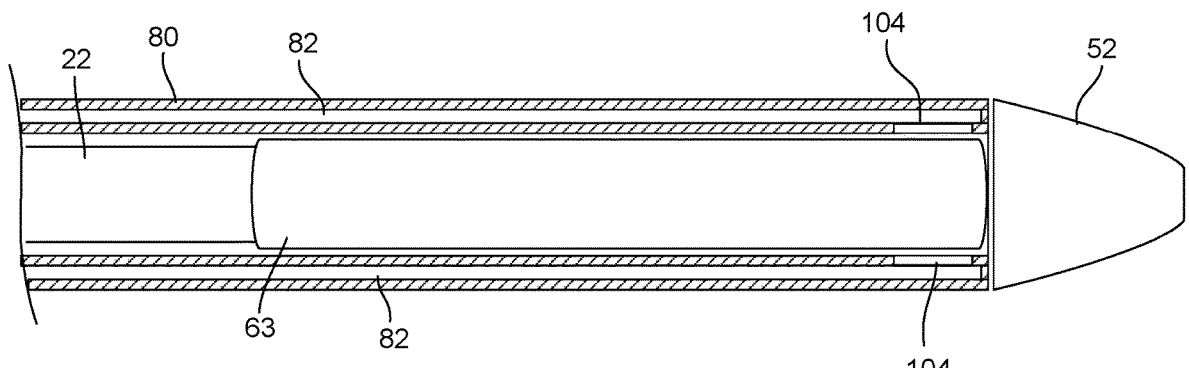

In yet another variation, FIG. 5C illustrates another variation in the partial cross-sectional view where a single enlarged opening 104 near or at the distal end of the sheath 80 along its inner surface may be defined. Rather than having multiple openings, a single enlarged annular opening 104 may be used to pass a relatively larger amount of drugs for infusion and coating upon the balloon surface. Alternatively, two or more relatively large openings positioned circumferentially along the inner surface of sheath 80 may be utilized.

Figure 5D:
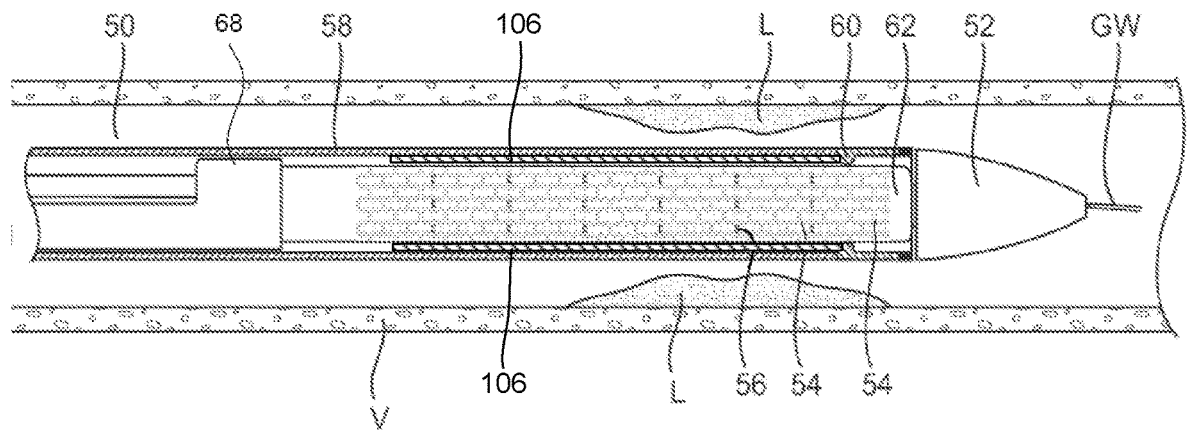
FIG. 5D shows a variation of a sheath having a drug or agent applicator attached along an inner surface of the sheath proximal to stent valve or separation element.

Another variation is illustrated in the partial cross-sectional side view of FIG. 5D, which illustrates sheath 58 having a drug or agent applicator 106 attached along an inner surface of the sheath proximal to stent valve or separation element 60. Applicator 106 may extend along a length of sheath 58 or stent valve 60 may be configured as a drug applicator itself. In variations where applicator 106 extends proximally of stent valve 60, applicator 106 may extend partially along sheath 58 the length of only one or more stent segments 54, or it may extend along a greater length of sheath 58 to cover many or all of stent segments 54. In either case, applicator 106 may be placed into contact with stent segments 54 and/or surface of balloon 62. In depositing the drug or agent upon the stent segments 54 and/or balloon 62, applicator 106 may be pre-loaded with the drug or agent such that the stent segments 54 and/or balloon 62 in contact with applicator 106 are coated. Moreover, stent segments 54 and/or balloon 62 may be further coated upon retraction of sheath 58 as applicator 106 is passed proximally over stent segments 54 and/or balloon 62. As mentioned, applicator 106 may be pre-loaded with the drug or agent prior to introduction into the vasculature. Alternatively, one or more drugs or agents may be introduced into or through applicator 106 by infusing the agents through one or more lumens defined through sheath 58 and directly into applicator 106.

Figure 5E:
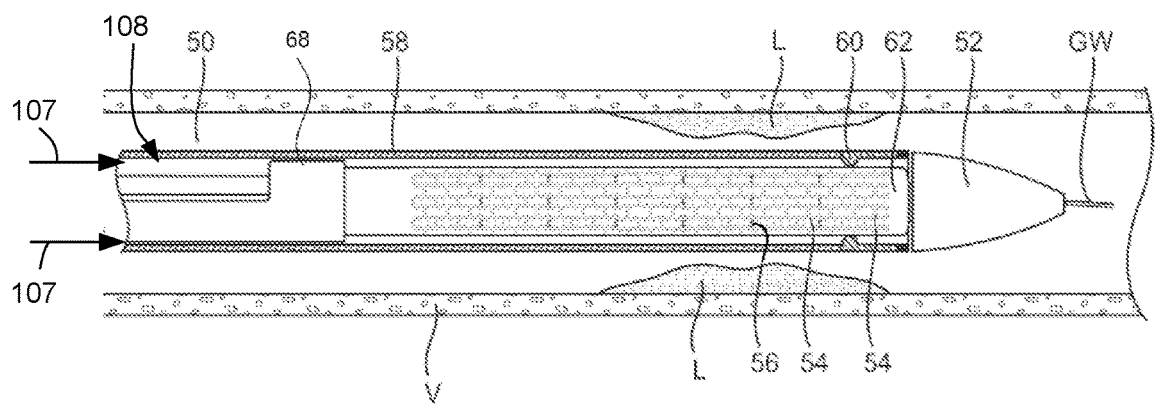
FIGS. 5E and 5F illustrate additional variations where the drug or agent may be infused directly through the handle from outside the patient body through the space between the sheath and balloon or through the space between the inflation lumen and pusher, respectively.
Figure 5F:
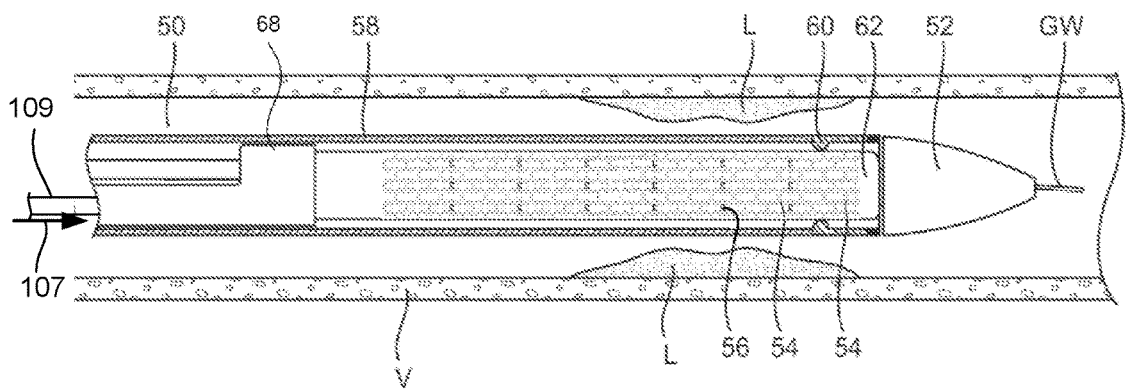

FIGS. 5E and 5F show partial cross-sectional side views of additional variations where rather than infusing the drug or agent through lumens defined within sheath 58 or via an applicator 106, the agents 107 may be infused directly through the handle from outside the patient body through the space 108 between sheath 58 and balloon 62, as shown in FIG. 5E. Alternatively, agents 107 may be infused through the space between inflation lumen 109 and pusher 68, as shown in FIG. 5F. In either case, with the infusion of the drugs or agents directly over the stent segments 54 and/or balloon 62, stent valve 60 may function as a seal to contain the agent within the sheath 58 and inhibit or prevent the leakage or escape of the agent into the vessel V.

Figure 6A:
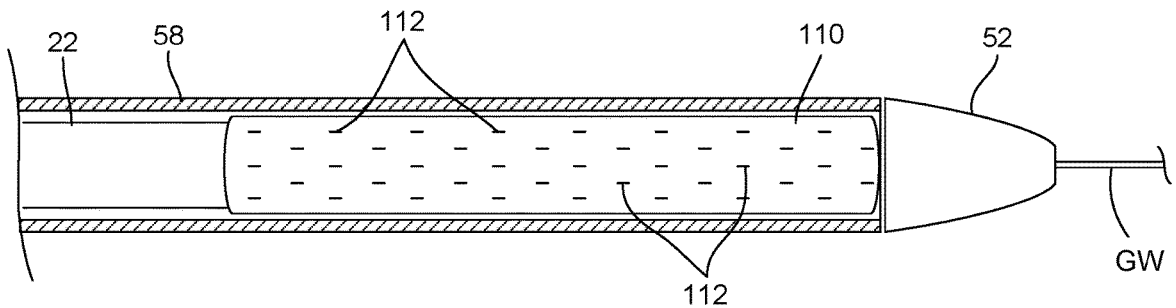
FIGS. 6A to 6C show another variation of a variably expandable balloon which defines a plurality of openings through which drugs may be delivered where the openings remain closed when the balloon is unexpanded but open when the balloon is expanded.
Figure 6B:
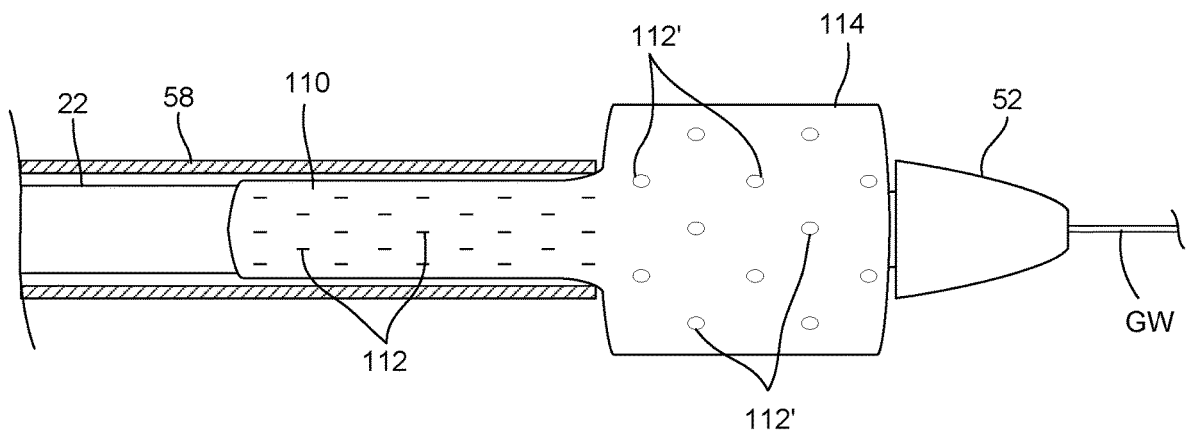
Figure 6C:
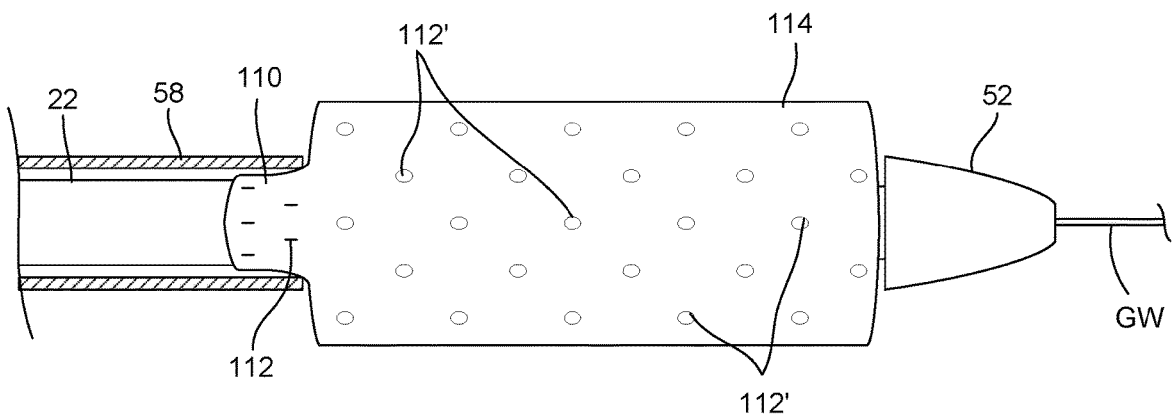

Other variations for a variably expandable balloon are shown in FIGS. 6A to 6C. FIG. 6A illustrates a balloon 110 in its unexpanded configuration and having a plurality of openings or pores 112 defined over the surface of the balloon 110 along its length. When unexpanded, the openings or pores remain closed along the balloon 110 to prevent the leakage of any drugs; however, when sheath 58 is retracted at least partially and balloon 110 is expanded, as shown in FIG. 6B, the openings or pores 112 may expand into an open configuration 112' along just the expanded portion 114 of the balloon 110 to allow for the infusion and release of the drugs from the widened openings 112'. The openings 112 may open in various ways including by the distension of the balloon material when under pressure during inflation, or by moving from a slit-shape to an ovular or circular opening as the balloon wall unfolds and/or expands. FIG. 6C shows an example of the sheath 58 further retracted to allow for a larger portion 114 of the balloon 110 to expand and to allow for the openings 112' to expand as well. In other variations, the openings or pores 112 may be open when the balloon 110 is deflated and remain open as the balloon 110 is expanded. In either case, the amount and dosage of the drug or agent passed through the openings will vary depending upon the type of drug or agent used as well as the amount of time the balloon is applied against the tissue. In one example, where a drug or agent such as Paclitaxel is injected through the openings 112, 1.2 mg in 10 ml having a pressure of 3 to 4 bar may be injected over a period of time, e.g., 60 seconds or as described above.

It should be noted that the use of the sheath over an inflatable balloon (particularly in embodiments without the use of stent segments) having a drug or agent deposited (or to be deposited) upon the balloon serves a number of unique purposes, including not only the controlled adjustment of the inflated balloon length, but the containment of the drug or agent upon the balloon, the protection of the drug or agent coating on the balloon surface to minimize loss or damage to the coating as the catheter is introduced through a vessel to the treatment site, and the controlled deposition of the drug or agent upon the balloon surface within the confines of the sheath, as well as other purposes described elsewhere herein.

Figure 7A:
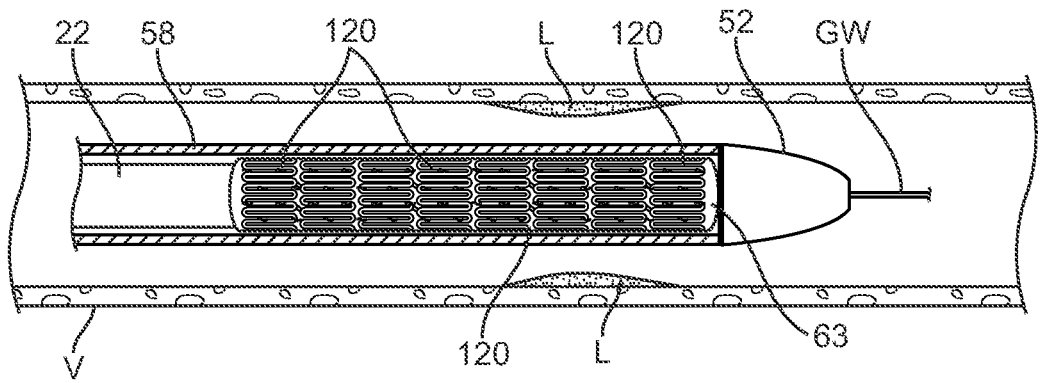
FIGS. 7A to 7C illustrate one method for delivering and placing a selected number of stent segments expanded via a balloon coated with a drug or agent.
Figure 7B:
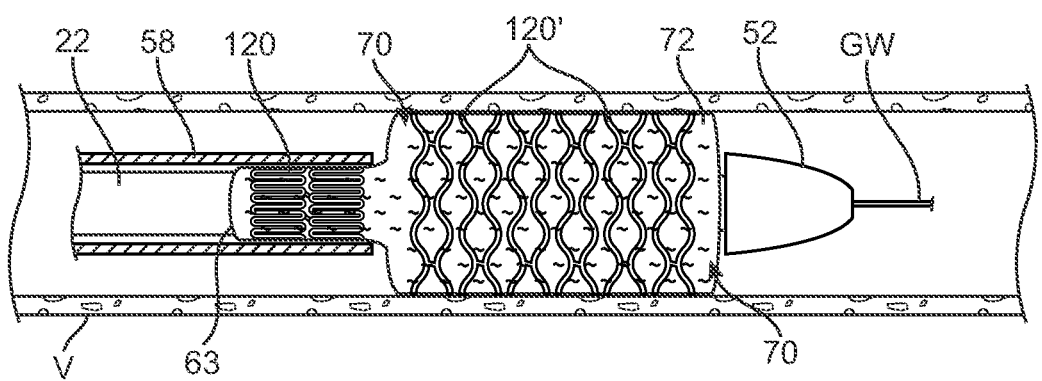
Figure 7C:
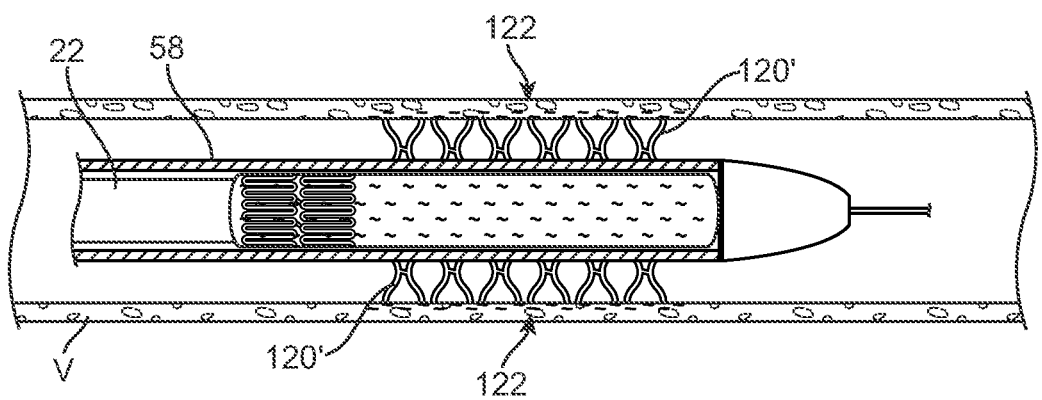

FIGS. 7A to 7C illustrate one example for delivering and placing a selected number of stent segments which are expanded via the variably expandable balloon coated with a drug or agent. FIG. 7A shows a partial cross-sectional view of the catheter advanced within vessel V and positioned proximate to or adjacent to a lesion L to be treated. In this variation, balloon 63 may be an expandable balloon coated or otherwise infused with any one or more of the agents or drugs 70 mentioned above. Alternatively, the retractable sheath may comprise a variation through which the one or more drugs may be infused through for depositing upon the balloon (and stent segment) surface. Once the appropriate number of stent segments 120 has been determined for adequately treating the lesion L, the sheath 58 may be retracted to expose the desired number of stent segments. As the stent segments 120' are expanded by balloon 63 into contact against the vessel walls, the expanded portion 72 of the balloon may also contact the vessel wall between the stent struts, as shown in FIG. 7B, to deposit the drug 70 from the balloon surface onto the vessel wall and/or on the surfaces of stent segments 120', as indicated by deposited drug 122 shown in FIG. 7C.

In delivering the one or more stent segments, multiple agents may be delivered not only by the balloon but also by the stent segments as well. For example, a restenosis inhibitor and either or both an endothelial cell promoter, attractor, or seeding agent may be coated or carried on the stent segments themselves as well as delivered via the balloon. In other variations, the restenosis inhibitor and/or endothelial cell promoter, attractor, or seeding agent, may be delivered in combination with a thrombus inhibitor (e.g., Plavix-Clopidogrel). As above, all (or any combination thereof) could be coated or carried on the stent segments or delivered via the balloon. The restenosis inhibitor may be carried on the outside surfaces of the stent segments for direct placement against the vessel wall when the stent (or stents) is expanded while the other agents may be carried on the inside and/or side surfaces of the stent struts. The stents may be coated with a material that attracts and/or retains the agents delivered by the balloon. Moreover, these agents could also be delivered several days, weeks, or months after the initial stent implantation.

Figure 8A:
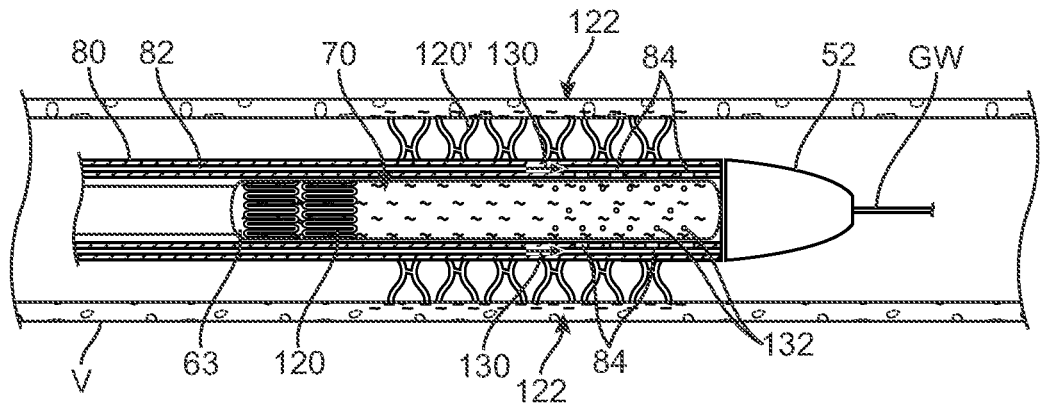
FIGS. 8A to 8C illustrate another method where one or more additional agents may be infused and placed onto the balloon surface in vivo for application upon the vessel wall and/or stent.
Figure 8B:
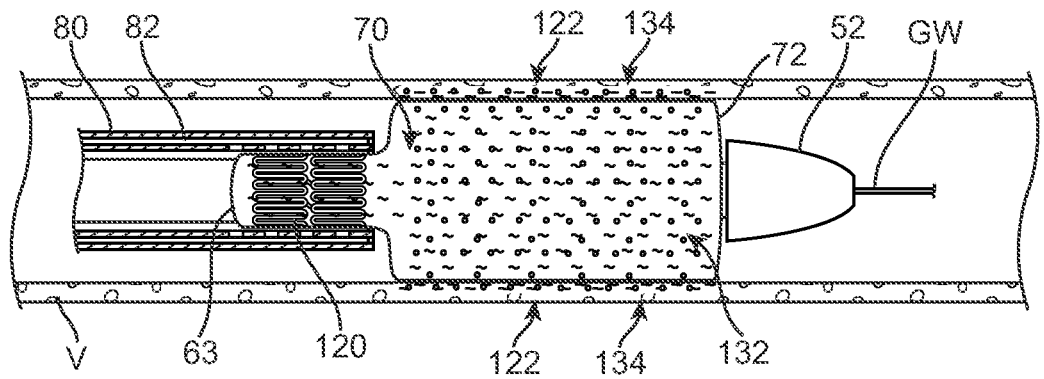
Figure 8C:
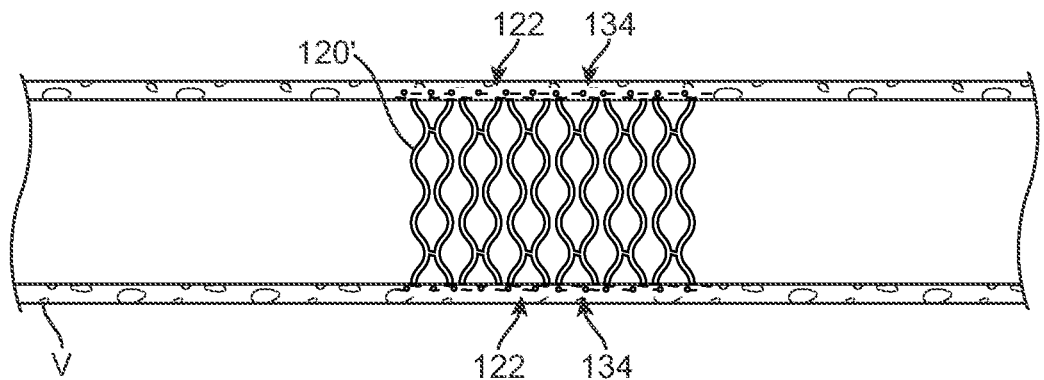

In another variation, one or more additional agents 130 may be deposited onto the balloon surface in vivo for application upon the vessel wall and/or stent segments. In this variation, sheath 80 may define the drug delivery lumen 82 for infusion through a plurality of openings 84 onto the balloon surface. A first drug 70, e.g., Biolimus A9 or any of the drugs mentioned above, may be deposited on the balloon 63 which may be expanded into contact against the vessel wall while deploying the expanded stent segments 120', thereby delivering the first drug 122 to the vessel walls and stent segments 120', as described above. Sheath 80 may be placed back over the deflated balloon 63 and a second drug 130, which may be the same or different than the first drug, may be infused through lumen 82 and deposited 132 upon the balloon surface, as shown in FIG. 8A. The sheath 80 may be retracted a second time to allow the balloon to expand into contact against the vessel wall to deposit the second drug 132 upon the vessel wall, as shown in FIG. 8B. FIG. 8C illustrates the deposited first drug 122 and second drug 134 placed upon the vessel wall as well as the deployed stent segments 120'. In exemplary embodiments, the first drug may be a restenosis inhibitor while the second drug is an endothelial cell promoter or attractor, a thrombus inhibitor or anti-platelet agent, or a combination of those and/or other agents.

Figure 9A:
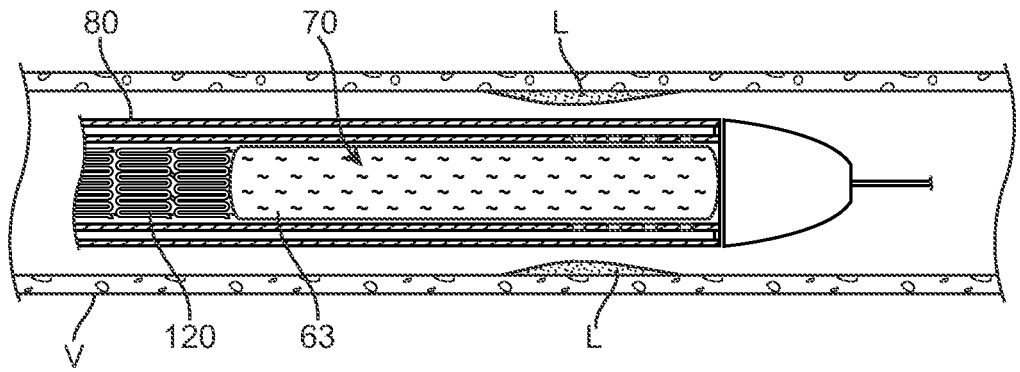
FIGS. 9A and 9B illustrate yet another method where a balloon having a first agent may be first expanded to apply the agent upon the vessel wall.
Figure 9B:
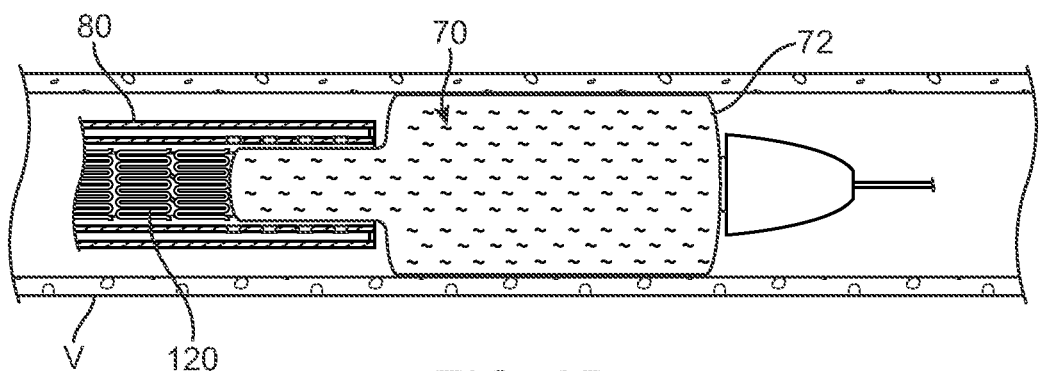

In yet another variation, an expandable balloon having a first agent may be expanded to first apply the agent upon the vessel wall prior to expanding the stent segments. As illustrated in FIG. 9A, the deployment catheter may be positioned intravascularly within vessel V proximate or adjacent to a lesion L to be treated. Balloon 63 may be coated with a first drug 70 and stent segments 120 may be initially positioned proximal to the balloon 63. Sheath 80 may be retracted by a desired distance sufficient to expose the appropriate balloon length for treating the lesion L and the balloon may be expanded 72 to contact the lesion L and vessel wall, as shown in FIG. 9B. Alternatively, rather than having balloon 63 initially coated with the first drug 70, the balloon may be coated by infusing the drug through the retractable sheath 80, as described above.

Figure 9C:
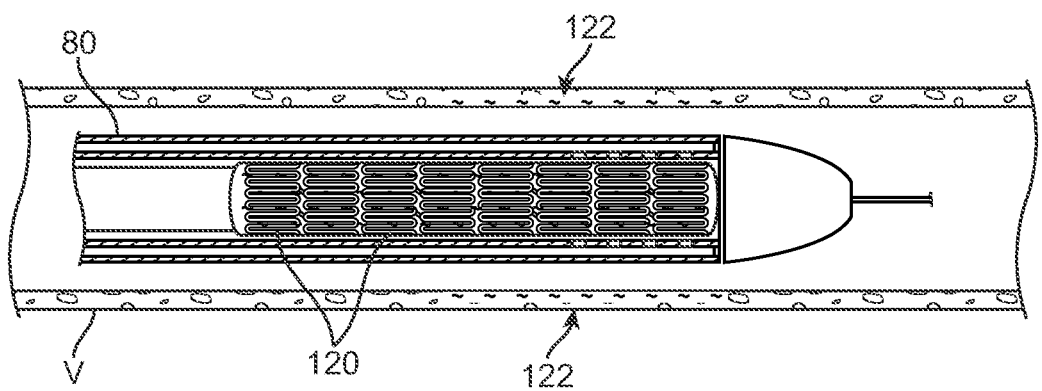
FIGS. 9C and 9D illustrate how a selected number of stent segments may be advanced over the balloon for expansion against the treated tissue wall.
Figure 9D:
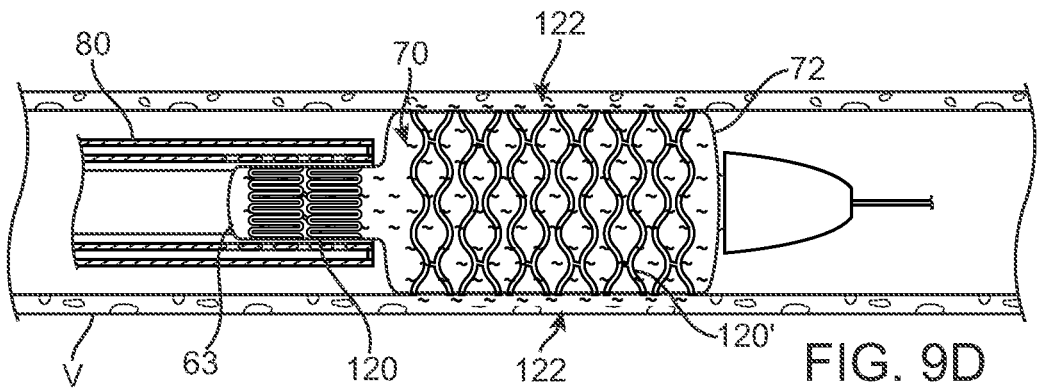
Figure 9E:
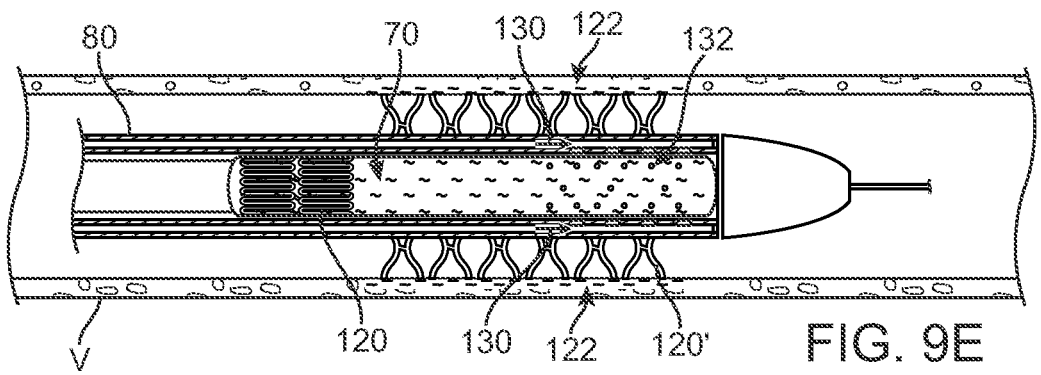
FIGS. 9E to 9G illustrate additional steps where an additional amount of the first agent or a second agent may be applied to the balloon in vivo such that the balloon can be expanded into contact against the previously expanded stent segments for treatment of the tissue wall with the additional agent.
Figure 9F:
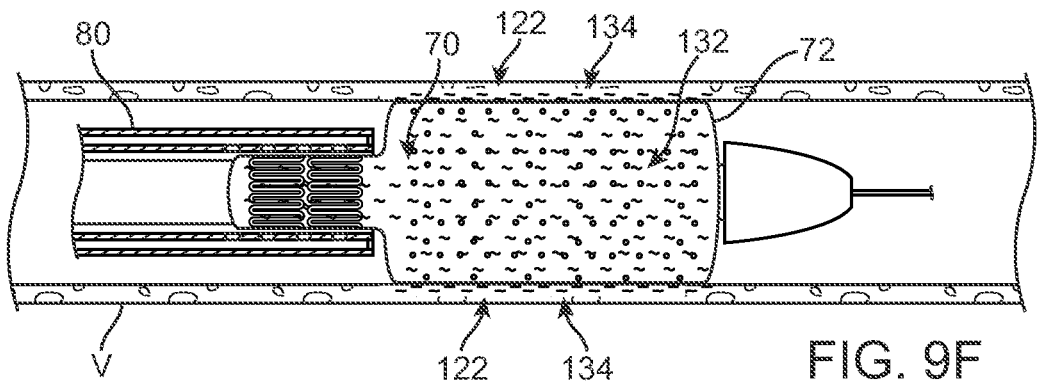
Figure 9G:
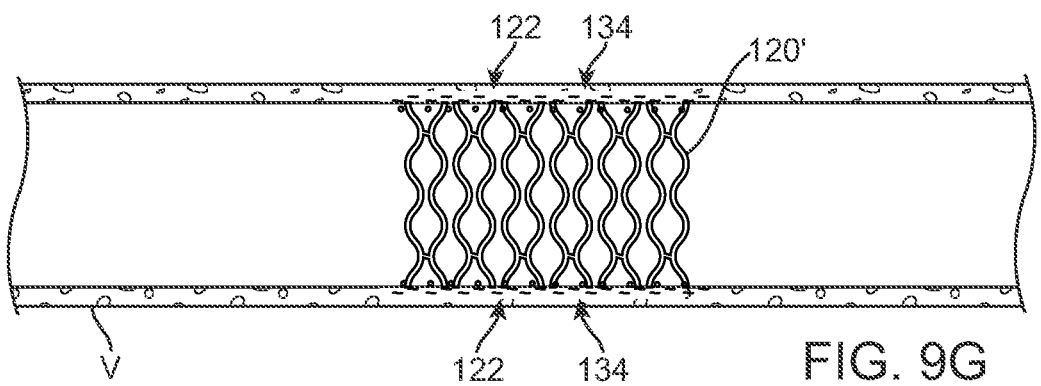

In either case, once the exposed length of balloon has been expanded into contact with the vessel wall, the balloon 72 may be deflated leaving the first drug 122 in the vessel wall. The stent segments 120 may then be pushed distally over the balloon via a pusher (not shown in this figure), as shown in FIG. 9C. With the vessel wall treated with the first drug 122, the sheath 80 may be retracted again to expose the appropriate number of stent segments 120 to be expanded 120' against the lesion L, as shown in FIG. 9D. Balloon 72 is then deflated and retracted again within sheath 80. A second drug 130 may optionally be infused via sheath 80 for infusion upon the deflated balloon surface, as shown in FIG. 9E. The sheath 80 is retracted again to expose the balloon now having a second drug 132 coated upon the exposed balloon surface and the balloon may be expanded again to contact the vessel wall and to deposit the second drug upon the tissue surface 134, as shown in FIG. 9F. With the vessel wall and expanded stent segments 120' treated with both the first 122 and second 134 drugs, the catheter may be repositioned in the same or a different vessel for treating another tissue region, as shown in FIG. 9G.

Figure 10A:
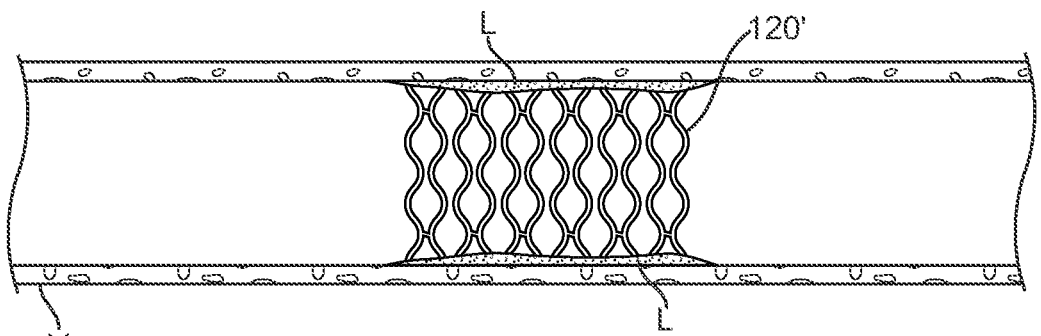
FIGS. 10A to 10D show another example where a drug-coated balloon may be positioned within a previously deployed restenosing stent and variably expanded to match the length of the stent and/or treatment region for application of a drug or agent upon the restenosing region.
Figure 10B:
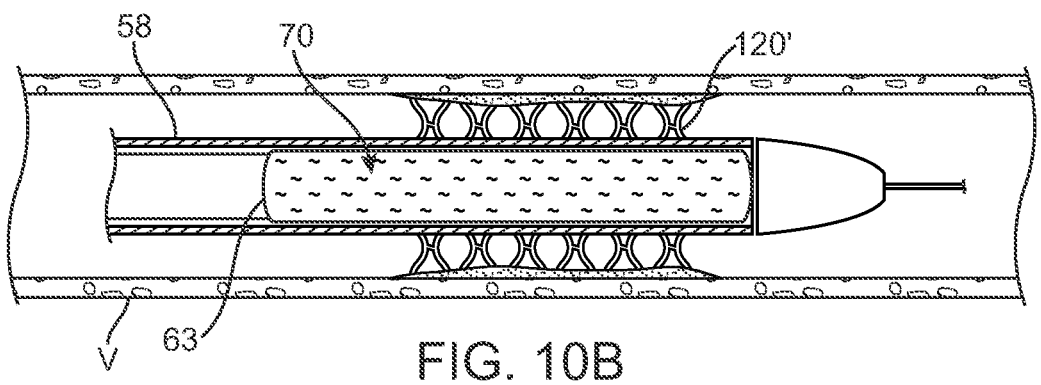

In yet another example for treatment, the variably expandable drug coated balloon may be utilized to treat a previously deployed stent. This may be useful where the previously deployed stent has become re-occluded from restenosis or where the previously deployed stent has not been fully covered by endothelial cells and thereby may be at risk of thrombus formation. As shown in FIG. 10A, a previously deployed stent 120' is illustrated within the vessel L. A catheter system having a drug coated balloon 63 may be advanced into the restenosing region of the vessel V, as shown in FIG. 10B. Balloon 63 may be coated in this variation with a drug which inhibits restenosis, e.g., Rapamycin, Everolimus, Biolimas A9, Paclitaxel, etc., or any of the other drugs or agents as mentioned above.

Figure 10C:
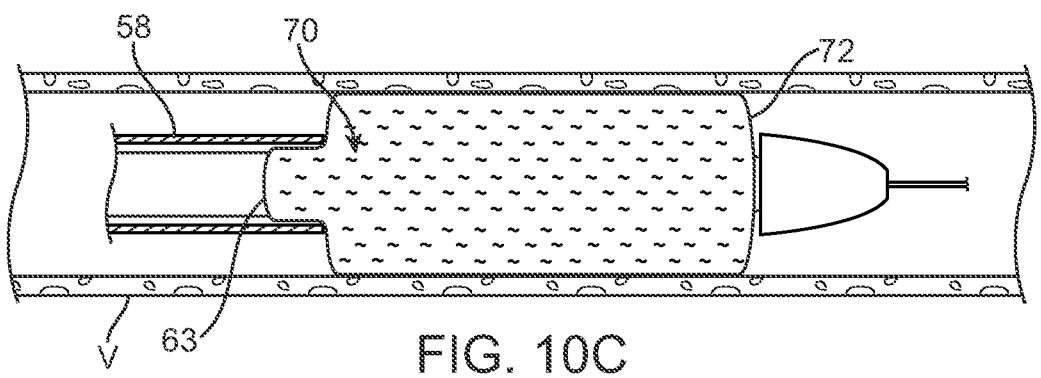
Figure 10D:
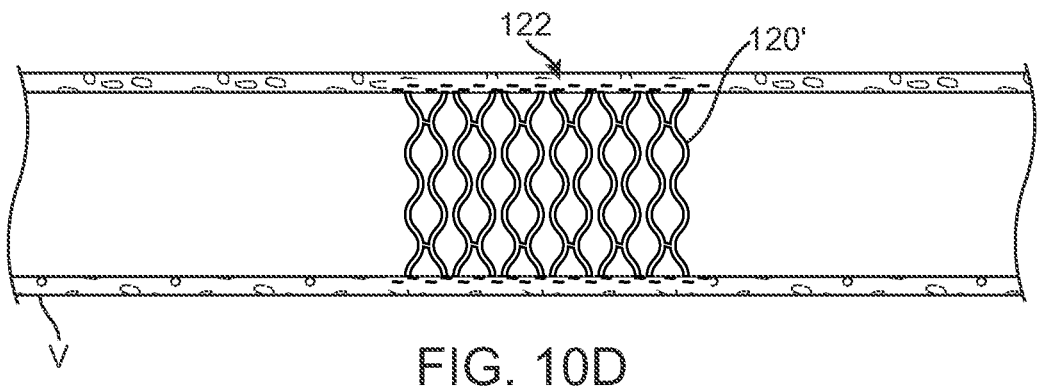

Once the variably expandable balloon has been exposed by sheath 58 to a desirable length which approximates the length of the restenosed region, balloon 63 may be expanded 72 to dilate the vessel and to apply the drug 70 onto the tissue wall, as shown in FIG. 10C. With the treatment completed, balloon 72 may be deflated and the catheter withdrawn from the region leaving the deployed stent 120' and vessel cleared of the stenosis and further leaving the drug 122 deposited upon the vessel wall and stent to further inhibit or prevent restenosis, as shown in FIG. 10D.

Figure 11A:
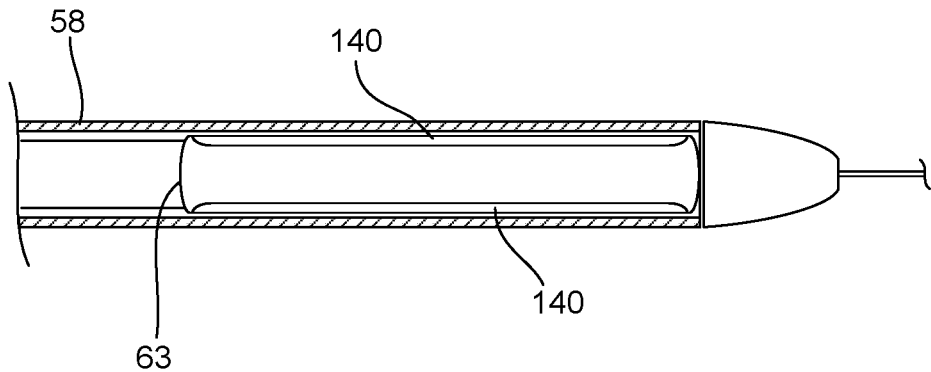
FIGS. 11A and 11B illustrate another variation where the variably expanded balloon may utilize a carrier coating upon its surface for delivering the one or more drugs against the tissue region.
Figure 11B:
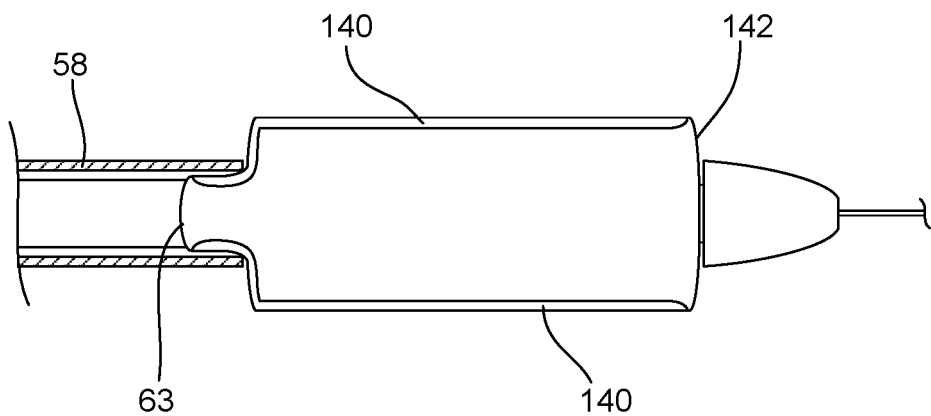

FIGS. 11A and 11B illustrate yet another variation where the variably expanded balloon 63 may utilize a carrier coating 140 disposed upon its surface for retaining the one or more agents to be delivered to the tissue region. As shown, the carrier coating 140 is sufficiently flexible and distensible to be expanded along its length by the balloon 142. The carrier coating 140 may be made from any number of polymeric materials, e.g., poly(lactide) (PLA), poly(glycolic acid) (P GA), poly(lactide-co-glycolide) (PLGA), and other polyhydroxyacids, polyethylene glycol (PEG), poly (caprolactone), polycarbonates, polyamides, polyanhydrides, polyamino acids, polyortho esters, polyacetals, degradable polycyanoacrylates and degradable polyurethanes, etc. Examples of natural polymers and materials include proteins such as albumin, collagen, fibrin, fibrinogen, hydroxyapatite (HAp), and synthetic polyamino acids, and polysaccharides such as alginate, heparin, and other naturally occurring biodegradable polymers of sugar units, etc. Other examples of polymeric materials are described in further detail in U.S. application Ser. No. 11/142,788 filed May 31, 2005 (U.S. Patent Publication US 2006/0271151 A1), which is incorporated herein by reference in its entirety. The carrier coating may be mixed or infused or coated by any of the one or more of the agents mentioned above for application against the vessel wall to be treated. Alternatively, the carrier coating may be disposed on top of a coating of the agent on the balloon, in which case the carrier coating may be a porous material which controls the rate of release of the agent from the balloon. Additionally, two, three, or more layers of carriers, polymers, primers, or therapeutic agents may be deposited on the balloon to achieve optimal adherence to the balloon, desired drug elution, timing and rate, and single or multiple agent delivery to the target tissue.

In still another alternative embodiment, the surface of the balloon may be roughened or coated with a layer containing microscopic pores or voids which can contain the agent and control its release at a suitable rate without the need for a polymer or other carrier material.

Figure 12:
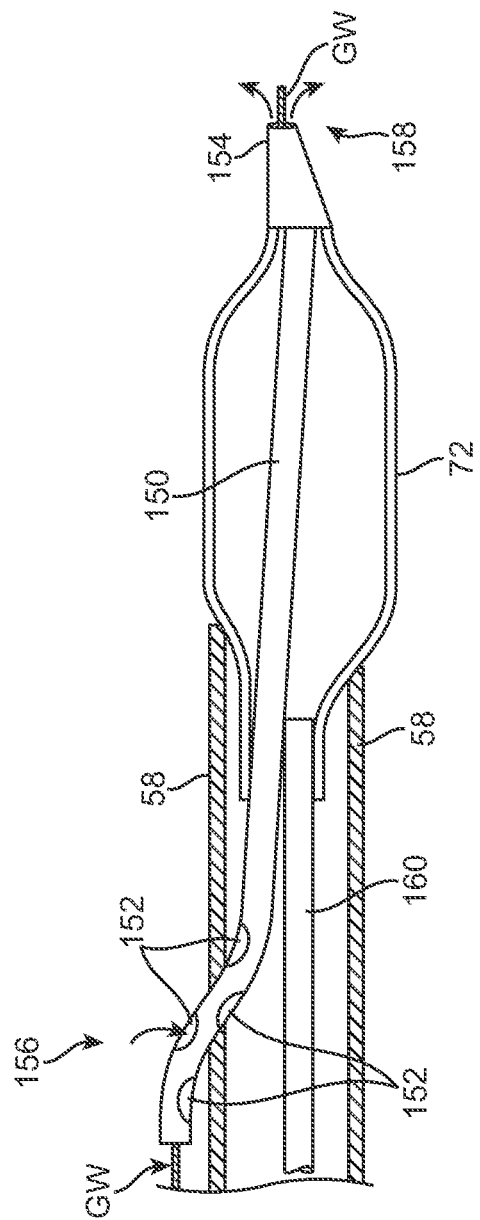
FIG. 12 shows another variation of a balloon catheter which includes a perfusion lumen extending from a first location proximal to the expanded balloon to a second location distal to the expanded balloon.

In yet another variation, FIG. 12 shows a balloon catheter which includes a perfusion lumen extending from a first location proximal to the expanded balloon to a second location distal to the expanded balloon. This catheter allows for blood to be shunted through the expanded balloon 72 via the perfusion lumen 150 to enable the blood flow to continue through the vessel, thereby allowing the balloon 72 to remain expanded for a sustained period of time so as to deliver the agent to the tissue walls longer for higher doses. The example shown illustrates perfusion lumen 150 (which may also function as a lumen for the passage of guidewire GW) passing through catheter sheath 58 and balloon 72 from a first location proximal to the inflated balloon 72 to a distal perfusion opening 154 at a second location distal to the inflated balloon 72. Perfusion lumen 150 may be adjacent to balloon inflation lumen 160.

With the expanded portion of the balloon 72 inflated and occluding blood flow through the vessel, blood may flow into perfusion lumen 150 through one or more perfusion openings 152 at the first location (illustrated by blood in-flow 156) and through balloon 72 to exit distal perfusion opening 154 at the second location distal to the inflated balloon 72 (illustrated by blood out-flow 158). The direction of blood flow through perfusion lumen 150 may, of course, be reversed depending upon the catheter orientation relative to the direction of blood flow. Once the appropriate amount of agents have been delivered to the vessel wall over a period of time, e.g., anywhere between 10 seconds to 10 minutes or preferably between 30 seconds to 150 seconds or more preferably about 60 seconds, the balloon may be deflated allowing for normal blood flow to resume through the vessel.

As described above, a drug or agent may be deposited upon the surface of the inflation balloon and/or stent segments or it may be infused in a controlled manner from one or more openings or pores distributed over the balloon surface for application upon the vessel walls. In additional variations, the drug or agent may be anchored upon the surface of the inflatable balloon and delivered to the surrounding tissue in a controlled manner to the surrounding tissue by activating the drug or agent in vivo either from within the vessel or extracorporeally by the use of electromagnetic radiation, e.g., visible, ultraviolet, infrared, near infrared, etc.

In one example for the controlled release of the drug or agent, nitric oxide (NO) in particular may be anchored or coated upon the balloon surface and irradiated by electromagnetic radiation having a wavelength, e.g., between 300 to 350 nm, to release between 1 and 100% NO into the surrounding tissue. As described in detail in U.S. Pat. No. 7,122,529 (Ruane et al.), which is incorporated herein by reference in its entirety, NO has been implicated in a variety of bioregulatory processes such as anticoagulation and vasodilation. In addition, NO is an effector molecule released by macrophages and other cells after immunological activation.

NO is synthesized from the amino acid L-arginine by an enzyme, NO synthase. It is believed that there are at least two forms of the enzyme: a constitutive form which releases NO for short periods in response to receptor or physical stimulation, and a second form which is induced after activation of macrophages, endothelial cells and certain other cells by cytokines and which, once expressed, synthesizes NO for extended periods.

The constitutive form of NO synthase is implicated in the transduction mechanism for soluble guanylate cyclase, and thus is involved in one of the mechanisms whereby cells regulate their own function or communicate with others. In addition, the release of NO in the cardiovascular system acts as a general adaptive mechanism whereby the vascular endothelium responds to changes in its environment and regulates blood flow and blood pressure through action on vascular smooth muscle. NO also regulates the interaction between the endothelium and the platelets; it may also play a role in the control of vascular smooth muscle proliferation.

Figure 13:
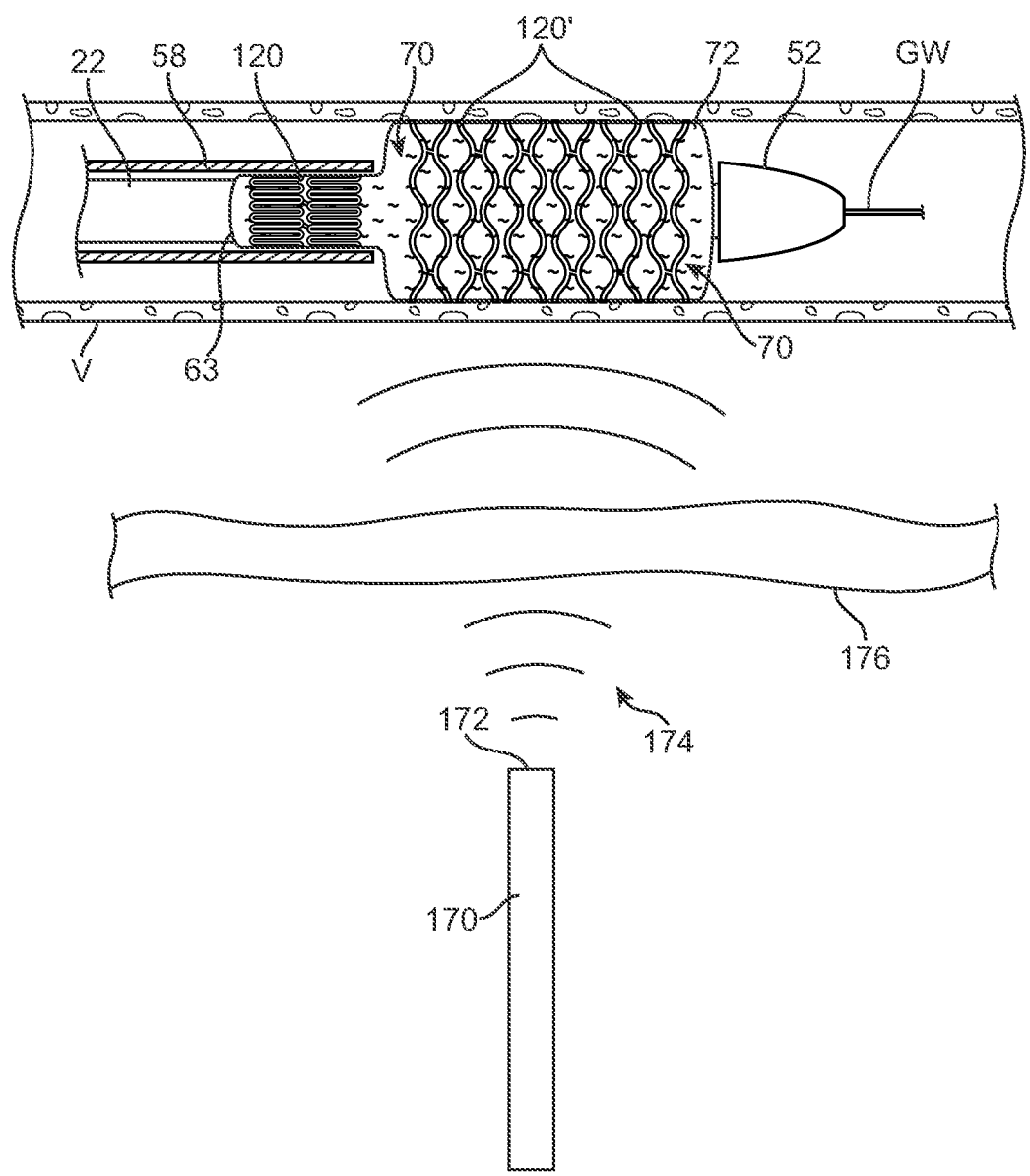
FIG. 13 shows an irradiation source emitted from an optical fiber extracorporeally to irradiate a drug or agent deposited within the underlying vessel to release an agent such as nitric oxide.

In controlling the release of NO from a balloon surface, an external source of electromagnetic radiation may be used to irradiate the stent such as a Nd:YAG. As shown in FIG. 13, an irradiation source such as optical fiber 170 coupled to an electromagnetic radiation source may emit, e.g., light 174, from its distal emitting tip 172 externally from the patient skin 176. As the wavelength is applied extracorporeally, the light 174 may be transmitted through the tissue to the underlying vessel V and incident upon the NO, as shown as drug or agent 70, where the transmitted light 174 may then activate the release of the NO upon the balloon 72 and/or upon the surrounding vessel walls.

Figure 14:
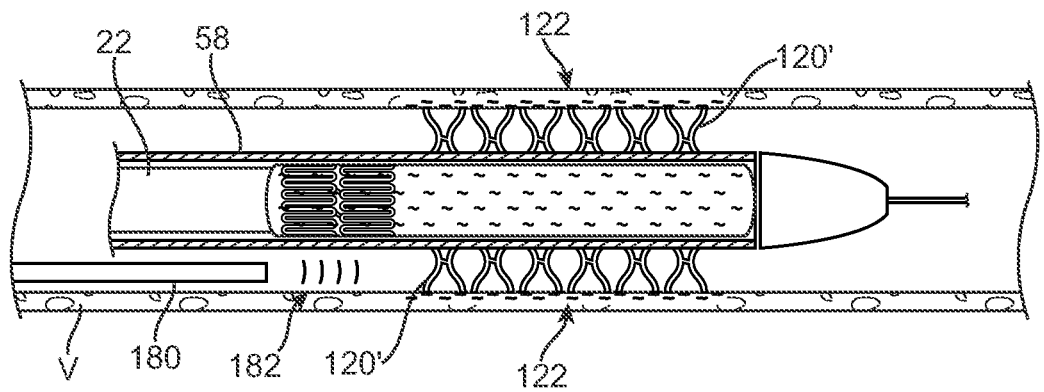
FIG. 14 shows an example of an optical fiber advanced intravascularly to irradiate the drug or agent.
Figure 15:
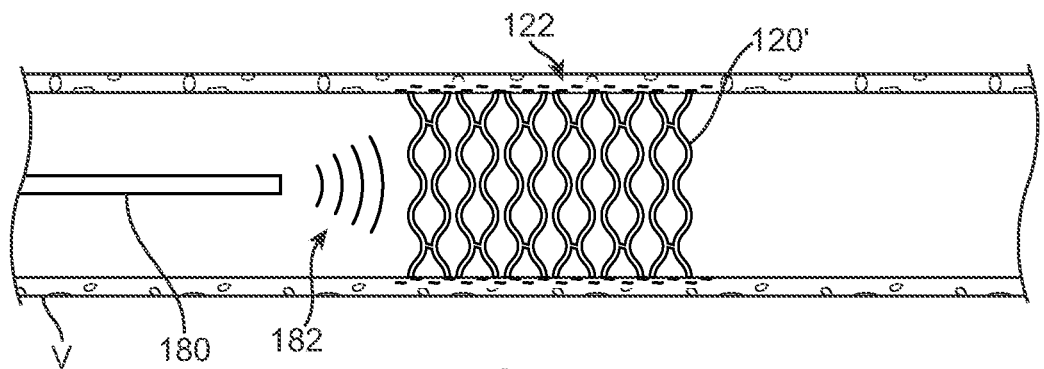
FIG. 15 shows another example of an optical fiber advanced intravascularly to irradiate the drug or agent where the deployment catheter has been removed.

Additionally and/or alternatively, a catheter carrying a flexible optical fiber 180 may be introduced into the patient body and advanced through the vessel V within or proximate to the region of tissue where the drug or agent 122 and/or stent segments 120' have been deployed, as shown in FIG. 14. Optical fiber 180 may then be used to irradiate the drug or agent deposited along the tissue and/or stent segments 120' with light 182 to activate the release of the drugs or agents. In yet another variation, the balloon catheter may be removed and the optical fiber 180 may be introduced separately and advanced to the area of treated tissue, where it may then emit the light 182 into the vessel V to activate the drugs or agents deposited upon the vessel walls and/or stent segments 120', as shown in FIG. 15. As in other embodiments, the balloon catheter of this embodiment may include a stent 120 as shown which may be deployed in conjunction with NO-delivery as the coated balloon is expanded, or which may be deployed in a separate balloon expansion after or before NO delivery via the balloon. Alternatively, the balloon catheter may carry no stents at all, and may be used solely for vascular dilatation and NO delivery via the coated balloon.

In yet another variation for controllably releasing drugs or agents, a hydrogel or carrier coating 140, as described above, which contains the drugs or agents may be deposited upon the balloon surface and/or surfaces of one or more stent segments. The hydrogel or carrier coating 140 may also contain a concentration of nanoparticles, e.g., nanoshells, having a layer of gold covering each nanoparticle. As the hydrogel or carrier coating 140 is contacted against or deposited upon the tissue wall to be treated, electromagnetic radiation, e.g., near infrared light, may be irradiated from within the vessel or extracorporeally upon the nanoparticle-containing hydrogel or carrier coating 140. The nanoparticles selectively absorb the radiation and convert it into heat which liquefies the hydrogel or carrier coating 140 allowing the drug or agent to be released into the tissue wall. A further description of nanoparticles and their uses are described in further detail in commonly owned U.S. Prov. Pat. App. 60/890,703 filed Feb. 20, 2007, which is incorporated herein by reference.

FIGS. 16A and 16B illustrate nanoshells having various outer shell thicknesses. Nanoshells are nanoparticles having a diameter ranging from a few nanometers up to about 5 microns. The nanoshells are composed of a non-conducting, semiconductor or dielectric inner core layer and an ultra thin conducting outer shell layer. In the exemplary embodiment of FIG. 16A, nanoshell 190 is spherically shaped and has an outer spherical shell 192 made from gold. A portion 194 of outer shell 192 has been removed in FIG. 16 A so that the inner spherical core 196 is visible. Inner core 196 is made from silicon dioxide. Other common materials that may be utilized for the inner core include, but are not limited to, gold sulfide, titanium dioxide, polymethyl methacrylate, polystyrene and macromolecules such as dendrimers. Metals which are well suited for use in the outer shell also include, but are not limited to silver, copper, platinum, palladium, lead, iron and the like. Nanoshells may be made with various inner core diameters and outer shell thicknesses. FIG. 16B illustrates another nanoshell 200 having a thinner outer shell 202 compared with the outer shell 192 of FIG. 16A. The nanoshell in FIG. 16B also has a section 204 of outer shell 202 removed so that the inner core 196 is visible.

Nanoshells have a unique ability to interact with specific wavelengths of electromagnetic radiation and effectively convert the incident radiation into heat energy. By adjusting the relative core and shell thicknesses, and choice of materials, nanoshells can be fabricated that will react with or scatter light at any wavelength across much of the ultraviolet, visible and infrared range of the electromagnetic spectrum. The nanoshell may therefore be tuned to specific wavelengths of electromagnetic radiation and the conversion of incident radiation to heat energy can be optimized.

FIG. 17 shows a graph 210 of the optical resonances of metal nanoshells having various ratios of core radius to shell thickness. In FIG. 17, nanoshells 212 and 214 both have a 60 nm inner core made from silicon dioxide. Nanoshell 212 has a gold outer shell, 20 nm thick and the resulting maximum absorption wavelength is approximately 740 nm. As the shell thickness decreases, the maximum absorption wavelength increases. Nanoshell 214 has a gold shell layer 5 nm thick and the resulting maximum absorption wavelength is approximately 1010 nm. The tunability of nanoshells, including the relationship between the ratio of core diameter to shell thickness and maximum absorption wavelength is more fully discussed in U.S. Pat. No. 6,344,272 which is incorporated herein by reference in its entirety.

Nanoshells are well described in the scientific and patent literature. Other aspects of nanoshells such as manufacturing methods, materials and principles of operation are described in U.S. Pat. Nos. 6,428,811; 6,530,944; 6,645,517; 6,660,381; 6,685,730; 6,699,724; 6,778,316; and 6,852,252, the entire contents of which are incorporated herein by reference in their entirety.

Because nanoshells are efficient at converting incident radiation into heat, they may be dispersed in hydrogel or carrier coating 140 and light or other forms of electromagnetic radiation may be used to heat up the hydrogel or carrier coating 140. Furthermore, since a nanoshell may be tuned to certain wavelengths, a nanoshell that preferentially interacts with light at near infrared wavelengths between approximately 700 and approximately 2500 nm is desirable, and more preferably between about 800 nm and 1200 nm, since this range of wavelengths is transmitted through tissue with very little absorption and therefore relatively little attenuation. Thus the majority of the light is delivered to the nanoparticles, converted into heat and transferred to the hydrogel or carrier coating 140 in which the nanoparticles are dispersed. This makes external access to an hydrogel or carrier coating 140 possible and heating of the tissue surrounding the implant is substantially avoided. One particular source of near infrared light, a Nd:YAG laser emits light at a wavelength of 1064 nm and hence is ideal for irradiating a hydrogel or carrier coating 140 from outside the body. Due to their small size, the nanoshells are easily purged by body systems such as the kidneys. Nanoshells therefore present a unique way of allowing a coating or implant to be heated from outside the body with minimal biocompatibility issues.

Although near infrared light is used to irradiate the nanoparticles and generate heat, it should be obvious to one of ordinary skill in the art that many wavelengths of electromagnetic radiation may also be used, including a magnetic field. The nanoparticles may be magnetically responsive so that they produce heat upon exposure to a magnetic field. Examples of magnetically responsive materials include iron oxides, magnetite ($Fe_3O_4$) and maghemite ($\gamma$-$Fe_3O_3$).

As shown in FIG. 18, balloon 142 having its adjustable inflation length may comprise the hydrogel or carrier coating 140 having a concentration 220 of nanoparticles and agents contained therein. As illustrated in the detail view, the hydrogel or carrier coating 140 contains the drugs or agents 224 along with the nanoparticles 222 to be applied against the tissue wall or stent segment surfaces. The incident radiation, which may be applied either intravascularly or extracorporeally (or both) as shown above, may heat the nanoparticles 222 to liquefy the hydrogel or carrier coating 140 to thereby release the drug or agents 222 in a controlled manner.

The applications of the devices and methods discussed above are not limited but may include any number of further configurations and treatments. Modification of the above-described assemblies and methods for carrying out the invention, combinations between different variations as practicable, and variations of aspects of the invention that are obvious to those of skill in the art are intended to be within the scope of the claims.

What is claimed is:

1. A balloon catheter, comprising:
   a catheter having an inflatable balloon positioned thereon;
   a sheath positioned over the balloon and which is axially movable with respect thereto, such that a length of an exposed and expandable portion of the balloon is adjustable, wherein the sheath defines at least one lumen therethrough in fluid communication between at least one opening defined along an inner surface of the sheath and a surface of the balloon; and
   at least one drug agent disposable through the at least one opening and upon at least the surface of the balloon.

2. The catheter of claim 1 wherein a non-exposed and non-expandable portion of the balloon is constrained from expansion within the sheath.

3. The catheter of claim 1 wherein the sheath further defines a plurality of openings along an inner surface of the sheath.

4. The catheter of claim 1 wherein the inflatable balloon defines a plurality of openings over its surface.

5. The catheter of claim 4 wherein the openings along the expandable portion of the balloon are sized to open from a closed configuration when the expandable portion is deflated to an open configuration when the expandable portion is inflated.

6. The catheter of claim 5 wherein the plurality of openings are in fluid communication with a reservoir.

7. The catheter of claim 1 further comprising a stent positionable over the balloon and expandable therewith.

8. A balloon catheter, comprising:
   a catheter shaft having an inflatable balloon positioned thereon;
   a sheath positioned over the balloon and which is axially movable with respect thereto, such that a length of an exposed and expandable portion of the balloon is adjustable, wherein the sheath defines at least one lumen therethrough in fluid communication between at least one opening defined along the sheath and a surface of the expandable portion of the balloon;
   at least one drug agent disposable through the at least one opening and upon at least the expandable portion of the balloon; and a seal incorporated on the sheath that inhibits or prevents the release of excess drug agent over the surface of the expandable portion of the balloon.

9. The catheter of claim 8 wherein the seal further facilitates even spreading of the at least one drug agent over the surface of the expandable portion of the balloon such that the at least one drug agent is more uniformly applied.

10. The catheter of claim 8 further comprising a stent having a total length carried within the sheath and a length adjustment mechanism adapted to adjust the length of an expandable portion of the stent which is less than the total length.

11. The catheter of claim 10 wherein the stent comprises a plurality of stent segments carried by the catheter shaft and movable longitudinally along the catheter shaft.

12. The catheter of claim 10 further comprising a positioner slidable longitudinally along the catheter shaft for moving a plurality of stent segments relative to the balloon from a first proximal position to a second position in which at least one of the stent segments surrounds the expandable portion of the balloon.

13. The catheter of claim 10 wherein the positioner comprises a sliding element configured to slide longitudinally along the catheter shaft and to push a plurality of stents distally along the catheter so as to move one of the stent segments adjacent to the balloon into a position in which it surrounds the balloon.

14. The catheter of claim 10 further comprising a perfusion lumen which passes through the catheter shaft from a first location proximal to the balloon to a second location distal to the balloon such that fluid is shunted through the perfusion lumen when the expandable portion of the balloon is inflated within a vessel.

15. A method of treating a region of a tissue wall, comprising:
    positioning a catheter having an inflatable balloon positioned thereon in proximity or adjacent to a region of the tissue wall;
    depositing at least one drug agent upon a surface of the balloon via a sheath;
    adjusting a position of the sheath with respect to the balloon such that an exposed portion of the balloon is coextensive with the region of tissue wall; and
    expanding the exposed portion of the balloon such that the at least one drug agent contacts the region of tissue wall.

16. The method of claim 15 wherein positioning the catheter comprises intravascularly advancing the catheter within a patient body.

17. The method of claim 15 wherein adjusting the position comprises retracting the sheath with respect to the balloon such that a distal end of the sheath overlies the balloon proximal to the exposed portion of the balloon.

18. The method of claim 15 wherein the at least one drug agent is delivered through a lumen in the sheath.

19. The method of claim 15 wherein depositing the at least one drug agent comprises delivering the at least one drug agent through a plurality of openings defined along an inner surface of the sheath upon the surface of the balloon.

20. The method of claim 15 further comprising positioning at least one stent segment over the balloon such that the at least one stent segment overlies the exposed portion of the balloon.

* * * * *